US008273405B2

(12) United States Patent
Feldstein et al.

(10) Patent No.: US 8,273,405 B2
(45) Date of Patent: Sep. 25, 2012

(54) WATER-ABSORBENT ADHESIVE COMPOSITIONS AND ASSOCIATED METHODS OF MANUFACTURE AND USE

(75) Inventors: Mikhail M. Feldstein, Moscow (RU); Danir F. Bairamov, Moscow (RU); Mikhail Borisovich Novikov, Moscow (RU); Valery G. Kulichikhin, Moscow (RU); Nicolai A. Platé, Moscow (RU); Gary W. Cleary, Los Altos Hills, CA (US); Parminder Singh, San Francisco, CA (US)

(73) Assignees: A.V. Topcheiv Institute of Petrochemical Synthesis, Russian Academy of Sciences, Moscow (RU); Corium International, Inc., Menlo Park, CA (US)

( * ) Notice: Subject to any disclaimer, the term of this patent is extended or adjusted under 35 U.S.C. 154(b) by 0 days.

(21) Appl. No.: 13/269,465

(22) Filed: Oct. 7, 2011

(65) Prior Publication Data
US 2012/0027695 A1 Feb. 2, 2012

Related U.S. Application Data

(63) Continuation of application No. 12/834,645, filed on Jul. 12, 2010, now abandoned, which is a continuation of application No. 11/028,702, filed on Jan. 3, 2005, now abandoned, which is a continuation-in-part of application No. 10/936,887, filed on Sep. 8, 2004, now abandoned, which is a continuation-in-part of application No. 10/359,548, filed on Feb. 5, 2003, which is a continuation-in-part of application No. 10/137,664, filed on May 1, 2002.

(60) Provisional application No. 60/288,008, filed on May 1, 2001.

(51) Int. Cl.
B05D 5/10 (2006.01)
A61K 8/18 (2006.01)
C08K 5/10 (2006.01)

(52) U.S. Cl. ........ 427/208; 523/111; 524/315; 524/316; 528/503; 424/49

(58) Field of Classification Search .................. 523/111; 524/315, 316; 528/503; 424/49; 427/208
See application file for complete search history.

(56) References Cited

U.S. PATENT DOCUMENTS

| | | |
|---|---|---|
| 2,561,071 A | 7/1951 | Prisk |
| 2,579,403 A | 12/1951 | Slomowitz et al. |
| 3,150,977 A | 9/1964 | Hart et al. |
| 3,689,439 A | 9/1972 | Field et al. |
| 3,721,657 A | 3/1973 | Seiderman |
| 3,749,755 A | 7/1973 | Bronstart et al. |
| 3,852,228 A | 12/1974 | Brothers |
| 3,957,605 A | 5/1976 | Assarsson et al. |
| 3,993,551 A | 11/1976 | Assarsson et al. |
| 3,996,934 A | 12/1976 | Zaffaroni |
| 4,091,090 A | 5/1978 | Sipos |
| 4,093,673 A | 6/1978 | Chang et al. |
| 4,160,020 A | 7/1979 | Ayer et al. |
| 4,231,369 A | 11/1980 | Sorensen et al. |
| 4,277,580 A | 7/1981 | Allen et al. |
| 4,325,851 A | 4/1982 | Colon et al. |
| 4,346,709 A | 8/1982 | Schmitt |
| 4,367,732 A | 1/1983 | Poulsen et al. |
| 4,492,685 A | 1/1985 | Keith et al. |
| 4,529,601 A | 7/1985 | Broberg et al. |
| 4,552,751 A | 11/1985 | Inaba et al. |
| 4,557,934 A | 12/1985 | Cooper |
| 4,562,060 A | 12/1985 | Broberg et al. |
| 4,568,343 A | 2/1986 | Leeper et al. |
| 4,587,289 A | 5/1986 | Comert et al. |
| 4,593,053 A * | 6/1986 | Jevne et al. ............. 523/111 |
| 4,624,665 A | 11/1986 | Nuwayser |
| 4,699,146 A | 10/1987 | Sieverding |
| 4,713,243 A | 12/1987 | Schiraldi et al. |
| 4,743,249 A | 5/1988 | Loveland |
| 4,750,482 A | 6/1988 | Sieverding |
| 4,771,105 A | 9/1988 | Shirai et al. |
| 4,849,224 A | 7/1989 | Chang et al. |
| 4,863,738 A | 9/1989 | Taskovich |
| 4,863,970 A | 9/1989 | Patel et al. |
| 4,867,748 A | 9/1989 | Samuelsen |
| 4,871,536 A | 10/1989 | Arraudeau et al. |
| 4,873,299 A | 10/1989 | Nowakowsky et al. |

(Continued)

FOREIGN PATENT DOCUMENTS

CA 2520986 4/2000

(Continued)

OTHER PUBLICATIONS

U.S. Appl. No. 11/150,811, filed Jun. 10, 2005, Feldstein et al.
U.S. Appl. No. 12/687,586, filed Jan. 11, 2009, Singh et al.
Aubin et al., "Analysis of the glass transition temperature of miscible polymer blends", Macromolecules, vol. 21, pp. 2945-2949, (1988).
Bairamov et al., "Kinetic parameters of poly(N-vinyl pyrrolidone) spontaneous mixing with short-chain poly(ethylene glycol)", Polym. Mater. Sci. Eng., vol. 82, vol. 82, pp. 7-8, (2000).
Borodulina et al. "Viscoelasticity of Pressure-sensitive adhesive and bioadhesive hydrogels under compressive load", Proceed. 24th Annual Meeting Adhesion Soc., pp. 147-149, (2001).

(Continued)

Primary Examiner — Tae H Yoon
(74) Attorney, Agent, or Firm — McDermott Will & Emery LLP; Susan T. Evans; Susan J. Myers Fitch

(57) ABSTRACT

An adhesive composition is provided that is water-insoluble yet water-absorbent, i.e., capable of absorbing up to 15 wt. % water or more. The composition in composed of a film-forming hydrophilic polymer with at least one linear segment having a plurality of recurring polar groups along the polymer backbone, a complementary multifunctional polymer with a plurality of recurring functional groups that noncovalently bind to the polar groups on the film-forming polymer, and plasticizer. A method for manufacturing the adhesive composition is provided as well.

16 Claims, 14 Drawing Sheets

U.S. PATENT DOCUMENTS

| | | |
|---|---|---|
| 4,877,628 A | 10/1989 | Stypula |
| 4,904,247 A | 2/1990 | Therriault et al. |
| 4,906,169 A | 3/1990 | Chien et al. |
| 4,927,408 A | 5/1990 | Haak et al. |
| 4,945,084 A | 7/1990 | Packman |
| 4,953,053 A | 8/1990 | Pratt |
| 4,973,468 A | 11/1990 | Chiang et al. |
| 4,983,395 A | 1/1991 | Chang et al. |
| 5,053,084 A | 10/1991 | Masumoto et al. |
| 5,053,227 A | 10/1991 | Chiang et al. |
| 5,057,500 A | 10/1991 | Thornfelt |
| 5,073,381 A | 12/1991 | Ivan et al. |
| 5,102,662 A | 4/1992 | Gallagher |
| 5,125,894 A | 6/1992 | Phipps et al. |
| 5,133,970 A | 7/1992 | Petereit et al. |
| 5,141,750 A | 8/1992 | Lee et al. |
| 5,173,302 A | 12/1992 | Holmblad et al. |
| 5,183,901 A | 2/1993 | Login et al. |
| 5,196,405 A | 3/1993 | Packman |
| 5,200,190 A | 4/1993 | Azuma et al. |
| 5,206,385 A | 4/1993 | Login et al. |
| 5,224,928 A | 7/1993 | Sibalis et al. |
| 5,232,702 A | 8/1993 | Pfister et al. |
| 5,234,690 A | 8/1993 | Chiang et al. |
| 5,234,957 A | 8/1993 | Mantelle |
| 5,240,995 A | 8/1993 | Gyory et al. |
| 5,254,346 A | 10/1993 | Tucker et al. |
| 5,270,358 A | 12/1993 | Asmus |
| 5,276,079 A | 1/1994 | Duan et al. |
| 5,296,512 A | 3/1994 | Beier et al. |
| 5,300,291 A | 4/1994 | Sablotsky et al. |
| 5,310,563 A | 5/1994 | Curtis et al. |
| 5,322,689 A | 6/1994 | Hughes et al. |
| 5,326,685 A | 7/1994 | Gaglio et al. |
| 5,332,576 A | 7/1994 | Mantelle |
| 5,338,490 A | 8/1994 | Dietz et al. |
| 5,342,623 A | 8/1994 | Enscore et al. |
| 5,344,394 A | 9/1994 | Gyory et al. |
| 5,354,823 A | 10/1994 | Tseng et al. |
| 5,362,420 A | 11/1994 | Itoh et al. |
| 5,376,377 A | 12/1994 | Gale et al. |
| 5,422,119 A | 6/1995 | Casper |
| 5,438,076 A | 8/1995 | Friedman et al. |
| 5,446,070 A | 8/1995 | Mantelle |
| 5,456,745 A * | 10/1995 | Roreger et al. ............ 106/140.1 |
| 5,462,743 A | 10/1995 | Turner et al. |
| 5,462,745 A | 10/1995 | Enscore et al. |
| 5,492,943 A | 2/1996 | Stempel |
| 5,508,024 A | 4/1996 | Tranner |
| 5,508,367 A | 4/1996 | Zajaczkowski |
| 5,527,271 A | 6/1996 | Shah et al. |
| 5,543,148 A | 8/1996 | Lapidus |
| 5,563,153 A | 10/1996 | Mueller et al. |
| 5,575,654 A | 11/1996 | Fontenot |
| 5,593,686 A | 1/1997 | Kissel et al. |
| 5,594,068 A | 1/1997 | Buchanan et al. |
| 5,599,373 A | 2/1997 | Zanuccoli |
| 5,614,178 A | 3/1997 | Bloon et al. |
| 5,631,267 A | 5/1997 | Gliech et al. |
| 5,633,010 A | 5/1997 | Chen |
| 5,641,504 A | 6/1997 | Lee et al. |
| 5,641,507 A | 6/1997 | DeVillez |
| 5,643,187 A | 7/1997 | Naestoft et al. |
| 5,645,062 A | 7/1997 | Anderson et al. |
| 5,645,855 A | 7/1997 | Lorenz |
| 5,656,286 A | 8/1997 | Miranda et al. |
| 5,660,178 A | 8/1997 | Kantner et al. |
| 5,662,925 A | 9/1997 | Ebert et al. |
| 5,663,010 A | 9/1997 | Stocchiero |
| 5,674,561 A | 10/1997 | Dietz et al. |
| 5,700,478 A | 12/1997 | Biegajski et al. |
| 5,702,721 A | 12/1997 | Horstmann et al. |
| 5,718,187 A | 2/1998 | Pollock et al. |
| 5,718,886 A | 2/1998 | Pellico |
| 5,719,197 A | 2/1998 | Kanios et al. |
| 5,723,145 A | 3/1998 | Shikinami et al. |
| 5,725,876 A | 3/1998 | Mantelle et al. |
| 5,726,250 A | 3/1998 | Zajaczkowski |
| 5,730,999 A | 3/1998 | Lehmann et al. |
| 5,744,155 A | 4/1998 | Friedman et al. |
| 5,762,956 A | 6/1998 | Chien et al. |
| 5,770,220 A | 6/1998 | Meconi et al. |
| 5,773,490 A | 6/1998 | Shikinami et al. |
| 5,780,050 A | 7/1998 | Jain et al. |
| 5,785,527 A | 7/1998 | Jensen et al. |
| 5,785,976 A | 7/1998 | Westesen et al. |
| 5,788,983 A | 8/1998 | Chien et al. |
| 5,800,832 A | 9/1998 | Tapolsky et al. |
| 5,804,611 A | 9/1998 | Takoh et al. |
| 5,827,213 A | 10/1998 | Jensen |
| 5,827,525 A | 10/1998 | Liao et al. |
| 5,830,932 A | 11/1998 | Kay |
| 5,837,713 A | 11/1998 | Gleich |
| 5,843,472 A | 12/1998 | Ma et al. |
| 5,846,558 A | 12/1998 | Nielsen et al. |
| 5,851,549 A | 12/1998 | Svec |
| 5,853,755 A | 12/1998 | Foldvari |
| 5,858,332 A | 1/1999 | Jensen et al. |
| 5,858,410 A | 1/1999 | Muller et al. |
| 5,863,662 A | 1/1999 | Hornby et al. |
| 5,876,746 A | 3/1999 | Jona et al. |
| 5,879,691 A | 3/1999 | Sagel et al. |
| 5,879,701 A | 3/1999 | Audett et al. |
| 5,891,453 A | 4/1999 | Sagel et al. |
| 5,894,017 A | 4/1999 | Sagel et al. |
| 5,900,249 A | 5/1999 | Smith |
| 5,902,598 A | 5/1999 | Chen et al. |
| 5,911,980 A | 6/1999 | Samour et al. |
| 5,912,271 A | 6/1999 | Brodin et al. |
| 5,916,587 A | 6/1999 | Min et al. |
| 5,942,543 A | 8/1999 | Ernst |
| 5,945,032 A | 8/1999 | Breitenbach et al. |
| 5,945,457 A | 8/1999 | Plate et al. |
| 5,948,416 A | 9/1999 | Wagner et al. |
| 5,948,430 A | 9/1999 | Zerbe et al. |
| 5,948,433 A | 9/1999 | Burton et al. |
| 5,958,379 A | 9/1999 | Regenold et al. |
| 5,958,446 A | 9/1999 | Miranda et al. |
| 5,962,011 A | 10/1999 | DeVillez et al. |
| 5,972,377 A | 10/1999 | Jona et al. |
| 5,976,565 A | 11/1999 | Fotinos |
| 5,985,311 A | 11/1999 | Cordes et al. |
| 5,985,860 A | 11/1999 | Toppo |
| 5,985,990 A | 11/1999 | Kantner et al. |
| 5,989,569 A | 11/1999 | Dirksing et al. |
| 5,990,179 A | 11/1999 | Gyori et al. |
| 5,993,836 A | 11/1999 | Castillo |
| 5,993,849 A | 11/1999 | Assmus et al. |
| 5,997,886 A | 12/1999 | Peffly et al. |
| 6,004,566 A | 12/1999 | Friedman et al. |
| 6,004,578 A | 12/1999 | Lee et al. |
| 6,007,837 A | 12/1999 | Enscore et al. |
| 6,024,976 A | 2/2000 | Miranda et al. |
| 6,045,811 A | 4/2000 | Dirksing et al. |
| 6,051,609 A | 4/2000 | Yu et al. |
| 6,063,399 A | 5/2000 | Assmus et al. |
| 6,068,650 A | 5/2000 | Hofmann et al. |
| 6,072,100 A | 6/2000 | Mooney et al. |
| 6,075,626 A | 6/2000 | Mizutani et al. |
| 6,083,421 A | 7/2000 | Huang et al. |
| 6,093,328 A | 7/2000 | Santina |
| 6,096,328 A | 8/2000 | Sagel et al. |
| 6,135,126 A | 10/2000 | Joshi |
| 6,142,939 A | 11/2000 | Eppstein et al. |
| 6,146,654 A | 11/2000 | Kubo |
| 6,153,215 A | 11/2000 | Samuelsen et al. |
| 6,162,456 A | 12/2000 | Dunbar et al. |
| 6,165,499 A | 12/2000 | Kleinsorgen et al. |
| 6,177,096 B1 | 1/2001 | Zerbe et al. |
| 6,193,993 B1 | 2/2001 | Murahashi et al. |
| 6,197,331 B1 | 3/2001 | Lerner et al. |
| 6,201,164 B1 | 3/2001 | Wulff et al. |
| 6,212,671 B1 | 4/2001 | Kanehira et al. |
| 6,221,341 B1 | 4/2001 | Montgomery |
| 6,221,383 B1 | 4/2001 | Miranda et al. |
| 6,231,885 B1 | 5/2001 | Carrara |
| 6,248,363 B1 | 6/2001 | Patel et al. |

| | | | | | | |
|---|---|---|---|---|---|---|
| 6,264,981 | B1 | 7/2001 | Zhang et al. | 2004/0053901 A1 | 3/2004 | Chien |
| 6,270,792 | B1 | 8/2001 | Guillemet et al. | 2004/0105834 A1 | 6/2004 | Singh et al. |
| 6,275,728 | B1 | 8/2001 | Venkatraman et al. | 2004/0136927 A1 | 7/2004 | Kim et al. |
| 6,306,370 | B1 | 10/2001 | Jensen et al. | 2004/0166147 A1 | 8/2004 | Lundy et al. |
| 6,312,666 | B1 | 11/2001 | Oxman et al. | 2004/0219111 A1 | 11/2004 | Kim et al. |
| 6,312,670 | B1 | 11/2001 | Montgomery | 2004/0258723 A1 | 12/2004 | Singh et al. |
| 6,316,022 | B1 | 11/2001 | Mantelle et al. | 2005/0031554 A1 | 2/2005 | Kim et al. |
| 6,322,774 | B1 | 11/2001 | Jensen et al. | 2005/0034905 A1 | 2/2005 | Singh et al. |
| 6,329,472 | B1 | 12/2001 | Kim et al. | 2005/0113510 A1 | 5/2005 | Feldstein et al. |
| 6,368,576 | B1 | 4/2002 | Jensen et al. | 2005/0208110 A1 | 9/2005 | Singh et al. |
| 6,419,905 | B1 | 7/2002 | Alvarez Hernandez | 2005/0215727 A1 | 9/2005 | Feldstein et al. |
| 6,419,906 | B1 | 7/2002 | Xu et al. | 2005/0228113 A1 * | 10/2005 | Baumer et al. ................ 524/500 |
| 6,451,240 | B1 | 9/2002 | Sherman et al. | 2005/0256223 A1 * | 11/2005 | Kolb et al. .................... 523/116 |
| 6,451,777 | B1 | 9/2002 | Bradbury et al. | 2006/0110434 A1 | 5/2006 | Yamaguchi et al. |
| 6,461,636 | B1 | 10/2002 | Arth et al. | 2006/0168905 A1 | 8/2006 | Blanc et al. |
| 6,488,913 | B2 | 12/2002 | Orlowski et al. | 2006/0171906 A1 | 8/2006 | Singh et al. |
| 6,517,350 | B2 | 2/2003 | Diasti et al. | 2006/0182788 A1 | 8/2006 | Singh et al. |
| 6,552,147 | B2 | 4/2003 | Parker et al. | 2006/0193793 A1 | 8/2006 | Kim et al. |
| 6,558,654 | B2 | 5/2003 | McLaughlin | 2006/0193794 A1 | 8/2006 | Kim et al. |
| 6,562,363 | B1 | 5/2003 | Mantelle et al. | 2008/0161492 A1 | 7/2008 | Cleary et al. |
| 6,576,712 | B2 | 6/2003 | Feldstein et al. | 2009/0258060 A1 | 10/2009 | Cleary et al. |
| 6,585,997 | B2 | 7/2003 | Moro et al. | | | |
| 6,591,124 | B2 | 7/2003 | Sherman et al. | FOREIGN PATENT DOCUMENTS | | |
| 6,596,298 | B2 | 7/2003 | Leung et al. | CA | 2402021 | 9/2001 |
| 6,602,912 | B2 | 8/2003 | Hsu et al. | CA | 2451431 | 1/2003 |
| 6,611,706 | B2 | 8/2003 | Avrahami et al. | CA | 2506073 | 6/2004 |
| 6,638,528 | B1 | 10/2003 | Kanios | DE | 8509793 | 5/1985 |
| 6,656,493 | B2 | 12/2003 | Dzija et al. | DE | 4219368 | 6/1992 |
| 6,667,410 | B2 | 12/2003 | Magnus et al. | EP | 0184470 | 6/1986 |
| 6,673,363 | B2 | 1/2004 | Luo et al. | EP | 0303445 | 2/1989 |
| 6,682,721 | B2 | 1/2004 | Kim et al. | EP | 0364211 | 4/1990 |
| 6,689,344 | B2 | 2/2004 | Chang et al. | EP | 0371421 | 6/1990 |
| 6,696,459 | B1 | 2/2004 | Jones et al. | EP | 0511782 | 11/1992 |
| 6,708,060 | B1 | 3/2004 | Avrahami et al. | EP | 0516026 | 12/1992 |
| 6,709,671 | B2 | 3/2004 | Zerbe et al. | EP | 0545594 | 6/1993 |
| 6,711,435 | B2 | 3/2004 | Avrahami | EP | 0581581 | 2/1994 |
| 6,714,497 | B2 | 3/2004 | Yeo et al. | EP | 0672094 | 9/1995 |
| 6,750,291 | B2 | 6/2004 | Kim et al. | EP | 0737477 | 10/1996 |
| 6,759,030 | B2 | 7/2004 | Kosti | EP | 0838225 | 4/1998 |
| 6,762,202 | B2 | 7/2004 | Marek et al. | EP | 0848960 | 6/1998 |
| 6,780,401 | B2 | 8/2004 | Kim et al. | EP | 1066823 | 1/2001 |
| 6,783,769 | B1 | 8/2004 | Arth et al. | GB | 1108837 | 4/1968 |
| 6,803,420 | B2 | 10/2004 | Cleary et al. | JP | 58-162681 | 9/1983 |
| 6,805,874 | B1 | 10/2004 | Lutz et al. | JP | 59-196817 | 11/1984 |
| 6,806,308 | B2 | 10/2004 | Zajac | JP | 01-151524 A | 6/1989 |
| 6,884,833 | B2 | 4/2005 | Cheang et al. | JP | 03-066612 | 3/1991 |
| 6,946,142 | B2 | 9/2005 | Chang et al. | JP | 03-247334 | 5/1991 |
| 6,962,691 | B1 | 11/2005 | Lulla et al. | JP | 03-275619 | 6/1991 |
| 7,078,359 | B2 | 7/2006 | Stepanian et al. | JP | 04-266818 | 9/1992 |
| 7,112,713 | B2 | 9/2006 | Sceusa | JP | 6-100467 | 4/1994 |
| 7,122,199 | B2 | 10/2006 | Sagel et al. | JP | 10-017448 | 1/1998 |
| 7,138,458 | B2 | 11/2006 | Cleary et al. | JP | 2001-213768 A | 7/2001 |
| 7,217,853 | B2 | 5/2007 | Kulichikhin et al. | JP | 2002-029949 | 1/2002 |
| 7,323,161 | B2 | 1/2008 | Choi et al. | JP | 2002-145746 A | 5/2002 |
| 7,384,650 | B2 | 6/2008 | Chien | KR | 20020045224 | 6/2002 |
| 7,456,331 | B2 | 11/2008 | Kulichikhin et al. | KR | 20030000299 | 1/2003 |
| 7,744,918 | B2 | 6/2010 | Yamaguchi et al. | KR | 20030000528 | 1/2003 |
| 2001/0006677 | A1 | 7/2001 | Mcginity et al. | KR | 20030003969 | 1/2003 |
| 2001/0021374 | A1 | 9/2001 | Montgomery | KR | 20030003973 | 1/2003 |
| 2001/0046471 | A1 | 11/2001 | Marek et al. | SU | 1459215 | 11/1995 |
| 2002/0004190 | A1 | 1/2002 | Diasti et al. | WO | WO 89/03859 | 5/1989 |
| 2002/0009420 | A1 | 1/2002 | McLaughlin | WO | WO 90/07940 A | 7/1990 |
| 2002/0048602 | A1 | 4/2002 | Flore et al. | WO | WO 94/05340 | 3/1994 |
| 2002/0076487 | A1 | 6/2002 | Zajac | WO | WO 96/19205 | 6/1996 |
| 2002/0106335 | A1 | 8/2002 | Orlowski et al. | WO | WO 97/11676 | 4/1997 |
| 2002/0131990 | A1 | 9/2002 | Barkalow et al. | WO | WO 98/20862 A1 | 5/1998 |
| 2002/0197284 | A1 | 12/2002 | Luo et al. | WO | WO 98/26763 | 6/1998 |
| 2003/0035841 | A1 | 2/2003 | Dzija | WO | WO 98/37870 | 9/1998 |
| 2003/0055190 | A1 | 3/2003 | Parker et al. | WO | WO 98/55044 | 12/1998 |
| 2003/0068376 | A1 | 4/2003 | Chen et al. | WO | WO 93/02717 | 2/1999 |
| 2003/0100654 | A1 | 5/2003 | Cheang et al. | WO | WO 99/11728 A1 | 3/1999 |
| 2003/0103427 | A1 | 6/2003 | Yeo et al. | WO | WO 99/17738 | 4/1999 |
| 2003/0152528 | A1 | 8/2003 | Singh et al. | WO | WO 99/44678 | 9/1999 |
| 2003/0152615 | A1 | 8/2003 | Houze et al. | WO | WO 99/47128 | 9/1999 |
| 2003/0170308 | A1 | 9/2003 | Cleary et al. | WO | WO 99/54422 | 10/1999 |
| 2003/0180229 | A1 | 9/2003 | Kosti | WO | WO 99/55312 A2 | 11/1999 |
| 2003/0225356 | A1 | 12/2003 | Kulichikhin et al. | WO | WO 00/16725 | 3/2000 |
| 2003/0235549 | A1 | 12/2003 | Singh et al. | WO | WO 00/18365 A2 | 4/2000 |
| 2004/0005277 | A1 | 1/2004 | Willison et al. | WO | WO 00/61120 A1 | 10/2000 |

| WO | WO 00/69421 | 11/2000 |
| WO | WO 01/01958 A1 | 1/2001 |
| WO | WO 01/07018 A1 | 2/2001 |
| WO | WO 01/26637 | 4/2001 |
| WO | WO 01/68045 | 9/2001 |
| WO | WO 01/87276 | 11/2001 |
| WO | WO 02/00182 A3 | 1/2002 |
| WO | WO 02/04570 | 1/2002 |
| WO | WO 02/087642 | 11/2002 |
| WO | WO 02/087645 | 11/2002 |
| WO | WO 02/089849 | 11/2002 |
| WO | WO 03/000216 | 1/2003 |
| WO | WO 03/099344 | 12/2003 |
| WO | WO 2004/045569 | 6/2004 |
| WO | WO 2004/054638 | 7/2004 |
| WO | WO 2004/071323 | 8/2004 |
| WO | WO 03/089046 | 10/2004 |
| WO | WO 2004/093786 | 11/2004 |
| WO | WO 2004/103201 | 12/2004 |
| WO | WO 2005/027768 | 3/2005 |
| WO | WO 2006/017807 | 2/2006 |
| WO | WO 2006/029407 | 3/2006 |
| WO | WO 2006/069236 | 6/2006 |
| WO | WO 2006/074173 | 7/2006 |
| WO | WO 2006/081497 | 8/2006 |
| WO | WO 2006/124639 | 11/2006 |
| WO | WO 2007/119656 | 10/2007 |
| WO | WO 2010/083035 | 7/2010 |

OTHER PUBLICATIONS

Chalykh et al., "Effects of composition and hydration on adhesive properties of poly($N$-vinyl pyrrolidone)-poly(ethylene glycol) hydrogels", Polym. Mater. Sci. Eng., vol. 81, pp. 456-457, (1999).
Chalykh et al., "Fracture mecahnics of poly($N$-vinyl pyrrolidone)-poly(ethylene glycol) hydrogel adhesive joints," Polym. Mater. Sci. Eng., vol. 81, pp. 427-428, (1999).
Chalykh et al., "Pressure-sensitive adhesion in the blends of poly($N$-vinyl pyrrolidone) and poly(ethlylene glycol) of disparate chain lengths," J. Adhesion, vol. 78, pp. 667-694, (2002).
Cleary et. al., A new polymer blend adhesive with combined properties to adhere to either skin or mucosa for drug delivery, podium abstract, 30th Annual Meeting and Exposition of the Controlled Released Society, Glasgow, Scotland, Jul. 19-23, 2003, Abstract #123.
Database WPI Section Ch, Week 198451, Derwent Publications Ltd., London, GB; AN 1984-315114 & JP 59196817A (Sekisuki Chem Ind Co Ltd) Nov. 8, 1984 abstract.
Database WPI Section Ch, Week 199150, Derwent Publications Ltd., London, GB; AN 1991-366353 & JP 03247334 A (Sumitomo Rubber Ind Ltd) Nov. 5, 1991 abstract.
Database WPI SEction Ch, Week 199118, Derwent Publications Ltd., London, GB; AN 1991-128478 & JP 03066612 A (Sato Pharm Co Ltd) Mar. 22, 1991 abstract.
Database WPI Section Ch, Week 199627, Derwent Publications Ltd., London, GB; AN 1996-266746 & SU 1459215 A (A Med CArdiology Res Centre) Nov. 20, 1995 abstract.
Emla Cream, (lidocaine 2.5% and prilocaine 2.5%), EMLA Anestetic Disc, (lidocaine 2.5% and prilocaine 2.5% cream), Topical adhesive system, Detailed prescription.
Feldstein et al., "A structure—property relationship and quantitative approach to the development of universal transdermal drug delivery system," NBC Risks, vol. 25, pp. 441-458, (1999).
Feldstein et al., "Coherence of thermal transitions in poly(N-vinly pyrrolidone)-poly(ethylene glycol) compatble blends; 1. Interrelations among the temperature of melting, maximum cold cyrstalization rate and glass transition", Polymer, vol. 41, pp. 5327-5338, (2000).
Feldstein et al., "Coherence of thermal transitions in poly($N$-vinyl pyrrolidone)—poly(ethylene glycol) compatible blends: 2. The temperature of maximum cold crystalization rate versus glass transition", Polymer, vol. 41, pp. 5339-5348, (2000).
Feldstein et al., "Coherence of thermal transition in poly($N$-vinyl pyrrolidone)—poly(ethylene glycol) compatible blends: 3. Impact of sorbed water upon phase behavior", Polymer, vol. 41, pp. 5439-5359, (2000).

Feldstein et al., "Correlations between activation energy for debonding and that for self-diffusion in pressure-sensitive hydrogels", Proceed. 24th Annual Meeting Adhession Soc., pp. 137-140, (2001).
Feldlstein et al. "Contribution of molecular mobility to debonding of pressure-sensitive adhesive hydrogels", Polym. Mater. Sci. Eng., vol. 81, pp. 467-468, (1999).
Feldstein et al., "Effect of hydrophillic matrix hydration of transdermal drug delivery kinetics: I. The matrix hydration In Vivo and In Vitro", Prediction of Percutaneous Penetration, vol. 4b, pp. 61-64, Brain, et al., (Eds.) (1996).
Feldstein et al., "Effect of hydrophilic matrix hydration on treansdermal drug delivery kinetics: II. In Vitro cytasine Delivery From Cypercuten TTS", Prediction of Percutaneous Penetration, vol. 4b, pp. 65-67, Brian, et al., (Eds.) (1996).
Feldstein et al., "Effect of hydrophilic matrix hydration on transdermal drug delivery kinetics: III. In Vitro clonide delivery from clopercuten TTS", Prediction of Percutaeous Penetration, vol. 4b, pp. 68-70, Brian, et al., (Eds.) (1996).
Feldstein et al., "Effect of hydrophilic matrix hydration on transdermal drug delivery kinetics: IV. In Vitro—In Vivo correlation." Prediciton of Percutaneous Penetration, vol. 4b, pp. 71-73, Brian, et al., (eds.) (1996).
Feldstein et al., "Effects of chains orientation, free volume and interaction on glass transition in poly($N$-vinyl pyrrolidone)—poly(ethylene glycol) blends involving a stoichiometric hydrogen-B bonded network complex", Polym. Mater. Sci. Eng., vol. 82, pp. 365-366, (2000).
Feldstein et al., "General approach to the molecular design of hydrophilic pressureu-sensitive adhesives," Proc. 25th Ann. Mtg. and 2nd World Congress on Adhesion and Related Phenomena, Orlando, FL, vol. 1, pp. 292-294 (2002).
Feldstein et al., "Molecular insight into rheological and diffusion determinants of pressure sensitive adhesion", Proceed. 23rd Annual Meeting Adhesion Soc., pp. 54-56, (2000).
Feldstein et al., "Peculiarities of glass transition temperature relation to the composition of poly($N$-vinyl pyrolidone) blends with short chain poly(ethylene glycol)", Polymer, vol. 42, pp. 7719-7726, (2001).
Feldstein et al., "Quantitative relationship between molecular structure and adhesion of PVP-PEG hydrogels", Polym. Mater. Sci Engl., vol. 81, pp. 465-466, (1999).
Feldstein et al., "Relation of glass transition temperature to the hydrogen bonding degree and energy in poly($N$-vinyl pyrrolidone) blends with hydroxyl-containing plasticizers: 2. Effects of poly(ethylene glycol) chain length", Polymer, vol. 42, pp. 981-990, (2001).
Feldstein et al., "Universal hydrophilic drug-containing adhesive matrix for systemic and topical transdermal drug delivery", Proc. 1st World Meeting APGI/APV, Budapest, Sep. 2011, 2 pages (1995).
Handbook of Pharmaceutical Excipients, Arther H. Kibbe, ed., 3rd ed., pp. 401-406, (2000).
Hawley's Condensed Chemical Dictionary, 14th Edition, Citation, "Oligomer, A polymer molecule of only a few monomer units (dimer, trimer, tetramer)", John Wiley and Sons, Inc., (2002).
International Search Report for PCT/US2000/18557 mailed Oct. 17, 2000.
International Search Report for PCT/US2001/21417 mailed Feb. 25, 2002.
International Search Report for PCT/US2002/13680 mailed Sep. 18, 2002.
International Search Report for PCT/US2002/14260 Mailed Sep. 17, 2002.
International Search Report for PCT/US2002/14725 mailed Sep. 27, 2002.
International Search Report for PCT/US2003/16408 Mailed Dec. 8, 2003.
International Search Report for PCT/US2003/039717 Mailed Jun. 28, 2004.
International Search Report for PCT/US2004/003443 Mailed Aug. 20, 2004.
International Search Report for PCT/US2004/011567 Mailed Jan. 10, 2006.
International Search Report for PCT/US2004/015448 Mailed Dec. 28, 2004.

International Search Report for PCT/US2004/029620 Mailed Jun. 1, 2005.
International Search Report for PCT/US2005/0002873 Mailed Apr. 27, 2005.
International Search Report for PCT/US2005/0034439 Mailed Jul. 19, 2006.
International Search Report for PCT/US2005/0046577 Mailed Jul. 26, 2006.
International Search Report for PCT/US2005/028063 Mailed Apr. 28, 2006.
International Search Report for PCT/US2005/032525 Mailed Mar. 17, 2006.
International Search Report for PCT/US2006/000098 Mailed Nov. 3, 2006.
International Search Report for PCT/US2006/0003091 Mailed Oct. 11, 2006.
International Search Report for PCT/US2006/018500 Mailed Sep. 21, 2006.
Kotomin et al., "Squeeze-recoil analysis of adhesive hydrogels and elastomers", Polym. Mater. Sci. Eng., vol. 81, pp. 425-426, (1999).
Kotomin et al., "Durability and fracture of some visceolastic adhesives," Proceed. of the 23rd Annual Meeting of the Adhesion Soc., pp. 413-415, (Feb. 20-23, 2000).
MSDS (Material Safety Data Sheet), Lactic Acid, No. L0522, (2008).
Patent Abstracts of Japan, vol. 017, No. 055 (C-1023) Feb. 3, 1993 & JP 04 266818 A (Sekisul Chem Co Ltd), Sep. 22, 1992 abstract.
Roos et al., "Probe tack investigation of poly(vinyl pyrrolidone)-poly(ethylene glycol) blends", Proceed. 24th Annual Meeting Adhesion Soc., pp. 277-279, (2001).
Schehlmann "Polyvinylcaprolactam: physical and cosmetic properties of a new hari fixative resin", Lecture, SOFW-Journal-Sounderdruck, 6 pages (1997).
Sintov et al., "Radiofrequency-driven skin microchanneling as a new way for electically assisted transdermal delivery of hydrophilic drugs", J. Contr.Release, vol. 89, pp. 311-320, (2003).
Supplementary European Search Report for EP04783729.9 Mailed Jun. 5, 2009.
Vartapian et al., "Self-diffusion in poly(N-vinyl pyrrolidone)-poly-(ethylene glycol) sytems", Colloid Polym. Sci., vol. 279, pp. 532-538, (2001).
Vartapian et al., "Molecular dynamics in poly(N-vinyl pyrrolidone)-poly(ethylene glycol) blends by pulsed-field gradient NMR method: effects of aging, hydration and PEG chain length", Macromol. Chem. Phys., vol. 202, pp. 2648-2652, (2001).

Barbucci et al. "Swelling behavior of carboxymethylcellulose hydrogels in relation to cross-linking, pH, and charge density", Macromolecules, vol. 33, No. 20, pp. 7475-7480 (2000).
Emla Cream, (lidocaine 2.5% and prilocaine 2.5%), EMLA Anesthetic Disc, (lidocaine 2.5% and prilocaine 2.5% cream), "Topical anesthetic for dermal analgesia", AstraZeneca Product Monograph, 46 pgs., Revised May 25, 2010.
EURDRAGIT® RL 100, "EUDRAGIT® RL 100 is a copolymer of ethyl acrylate, methyl methacrylate and a low content of methacrylic acid ester with quaternary ammonium groups. The ammonium groups are present as salts and make the polymers permeable", Product Information, Accessed online from: http://eudragit.evonik.com/product/eudragit/en/products-services/eudragit-products/sustained-release-formulations/rl-100/pp./default.aspx, 1 page, accessed on Apr. 15, 2011.
EUDRAGIT® RS 100, "EUDRAGIT® RS 100 is a copolymer of ethyl acrylate, methyl methacrylate and a low content of methacrylic acid ester with quaternary ammonium groups. The ammonium groups are present as salts and make the polymers permeable", Product information, Accessed online from: http://eudragit.evonik.com/product/eudragit/en/products-services/eudragit-products/sustained-release-formulations/rs-100/pages/default.aspx, 1 page, accessed on Apr. 15, 2011.
Evonic Industries, "EUDRAGIT® E 100: EUDRAGIT® E 100 is a cationic copolymer based on dimethylaminoethyl methacrylate, butyl methacrylate, and methyl methacrylate", Product Information, Accessed Online from http://eudragit.evonik.com, 1 page (2011).
Evonic Industries, "EUDRAGIT® L 12,5 and EUDRAGIT® S 12,5", Product Information, Accessed Online from http://eudragit.evonik.com, 1 page (2011).
Evonic Industries, "EUDRAGIT® RL 12,5 and EUDRAGIT® RS 12,5", Product Information, Accessed Online from http://eudragit.evonik.com, 1 page (2011).
Evonic Industries, "EUDRAGIT® NE 30 D: EUDRAGIT® NE 30 D is the aqueous dispersion of a neutral copolymer based on ethyl acrylate and methyl methacrylate", Product Information, Accessed Online from http://eudragit.evonik.com, 1 page (2011).
Feldstein et al., "A new class of pressure-sensitive adhesives based on interpolymer and polymer-oligomer complexes", Polymer Science, vol. 51, No. 7, pp. 799-814 (2009).
Whelan Polymer Technology Dictionary, Citation *Butyl Rubber*, Chapman Hall, 2-6 Boundry Row, London, UK, vol. 1, pp. 53 (1994).

* cited by examiner

WATER-ABSORBENT ADHESIVE COMPOSITIONS AND ASSOCIATED METHODS OF MANUFACTURE AND USE

CROSS-REFERENCE TO RELATED APPLICATIONS

This application is a continuation of U.S. patent application Ser. No. 12/834,645 filed Jul. 12, 2010, (now abandoned) which is a continuation of U.S. patent application Ser. No. 11/028,702 filed Jan. 3, 2005, (now abandoned), which is a continuation-in part of U.S. patent application Ser. No. 10/936,887, filed Sep. 8, 2004, (now abandoned), which is a continuation-in-part of U.S. patent application Ser. No. 10/359,548, filed Feb. 5, 2003, which is a continuation-in-part of U.S. patent application Ser. No. 10/137,664, filed May 1, 2002, which claims priority under 35 U.S.C §119(e)(1) to provisional U.S. Patent Application Ser. No. 60/288,008, filed May 1, 2001. The contents of which are incorporated herein in their entireties.

TECHNICAL FIELD

This invention relates generally to adhesive compositions, and more particularly relates to water-absorbent adhesive compositions composed of polymer blends. The invention additionally relates to methods for formulating such compositions, including methods for selecting components for inclusion in the compositions, to methods for using the compositions, and to products manufactured with the compositions. The invention finds utility in any context requiring an adhesive composition that adheres to a moist surface and neither dissolves nor loses tack upon absorption of water.

BACKGROUND

Hydrophilic adhesives, particularly hydrophilic pressure-sensitive adhesives ("PSAs"), are used in a wide variety of commercially significant products, including drug delivery systems, wound dressings, bioelectrodes, tooth-whitening systems, and the like. A general distinctive feature of hydrophilic PSAs is that they typically adhere to wet substrates, while conventional hydrophobic (rubber-based) PSAs typically lose their adhesive properties when moistened.

It is important to be able to modify the adhesive properties of a PSA according to intended use, as different applications can require very different adhesion profiles. For instance, the skin contact adhesive layer of a transdermal drug delivery system, or "patch," should provide for immediate adhesion following application of the patch to the skin and continued adhesion during an extended drug delivery period. As another example, delivery systems for application to wet surfaces, e.g., the buccal mucosa or the teeth, do not need to adhere to dry surfaces but should become tacky when applied to a hydrated or moistened surface. In another application, adhesive compositions used in wound dressings must become substantially nontacky following absorption of wound exudates to avoid tissue damage upon removal.

A method has recently been developed for tailoring the adhesive properties of polymer compositions useful in a number of applications, including pharmaceutical and cosmetic products. The method is based on new insights into the molecular mechanisms underlying adhesive properties, See, for example, Feldstein et al, (1999) *Polym. Mater. Sci, Eng.,* 81:465-466; Feldstein et al., *General approach to the molecular design of hydrophilic pressure-sensitive adhesives*, Proceed. 25th Annual Meeting Adhesion Soc. and $2^{nd}$ World Congress on Adhesion and Relative Phenomena, February 2002, Orlando, Fla., vol. 1 (Oral Presentations), p. 292-294; and Chalykh et al. (2002) *J. Adhesion* 78(8):667-694. As discussed in the foregoing references, pressure-sensitive adhesion results from the coupling of two apparently incompatible types of molecular structures, and there is a fine balance between strong cohesive interaction energy and enhanced "free volume."

That is, enhanced free volume in the molecular structure of a PSA polymer composition correlates with high tack exhibited at the macroscopic level and a liquid-like fluidity of the PSA material, which, in turn, allow for rapid formation of an adhesive bond. The "cohesive interaction energy" or "cohesion energy" defines the cohesive toughness of the PSA composition and provides the dissipation of detachment energy in the course of adhesive joint failure. Based on these findings, a general method for obtaining novel hydrophilic adhesives was developed and is described in U.S. Pat. No. 6,576,712 to Feldstein et al. In one embodiment, that method involves physically mixing a non-adhesive, hydrophilic, high molecular weight polymer with a relatively low molecular weight plasticizer capable of crosslinking the polymer via hydrogen bonding.

In PSAs, the molecular structures of the components dictate the cohesion energy and free volume, and thereby define the adhesive properties of the composition as a whole. For instance, in acrylic PSAs, strong cohesive interaction energy is a result of hydrophobic attraction between alkyl groups in side chains, whereas large free volume results from either electrostatic repulsion of negatively charged carboxyl groups or a significant number of isoalkyl radicals in the side chains. In synthetic rubbers, large free volume is obtained by adding high volume, low density tackifying resins. In hydrophilic adhesives, when a high molecular weight polyvinyl lactam, poly(N-vinyl-2-pyrrolidone) ("PVP") or polyvinyl caprolactone ("PVCap"), is blended with a polyethylene glycol ("PEG") oligomer, as described in U.S. Pat. No. 6,576,712, high cohesive strength results from the hydrogen bonding interaction between the oxo (=O) moieties of the pyrrolidone or caprolactone ring and the terminal hydroxyl groups of the PEG oligomer, while enhanced free volume is results from the spacing between polymer chains provided by the PEG bridges and the flexibility of the PEG oligomers.

Accordingly, the balance between cohesive energy and free volume, as described in the '712 patent, is in large part responsible for the adhesive properties of polymer materials. For instance, the ratio between cohesion energy and free volume dictates the glass transition temperature, $T_g$, and elastic modulus, E, of a polymeric material. That is, a composition with higher cohesion energy and lower free volume will have both a higher $T_g$ and a higher E.

When dry, the adhesive compositions described in U.S. Pat. No. 6,576,712, e.g. blends of high molecular weight PVP and low molecular weight PEG, exhibit relatively low adhesion toward dry surfaces. Adhesion increases, however, when the surface of a substrate is moistened or the adhesive composition absorbs water. The maximum adhesion of the PVPPEG blends described in the '712 patent is observed when the adhesive contains 5-10 wt. % of absorbed water (i.e., when water represents about 5 wt. % to about 10 wt. % of the moistened adhesive composition). This is usually the case when the adhesive is exposed to an atmosphere having 50% relative humidity (rh). When in direct contact with water, the adhesive dissolves. Therefore, the compositions are not optimal in applications wherein an adhesive composition is likely to undergo a significant degree of hydration during use, absorbing on the order of 15 wt. % water or more.

Accordingly, there is a need in the art for water-insoluble adhesive compositions that adhere well to moist surfaces even after absorbing a significant amount of water.

SUMMARY OF THE INVENTION

The invention is addressed to the aforementioned need in the art, and provides a water-insoluble adhesive composition that adheres well to moist surfaces even after absorbing a significant amount (e.g., greater than 15 wt. %) water. The invention also provides a method for preparing such a water-soluble adhesive composition.

In one embodiment, then, a method for preparing a water-insoluble, water absorbent adhesive composition is provided that comprises combining, under conditions effective to form a substantially homogeneous admixture:

(a) a film-forming, hydrophilic polymer comprising at least one linear segment containing a plurality of recurring polar groups;

(b) a complementary multifunctional polymer containing a plurality of recurring functional groups along the polymer backbone, said recurring functional groups capable of non-covalently binding to the recurring polar groups so that a ladder-like interpolymer complex is formed between the at least one linear segment and the complementary multifunctional polymer; and (c) a plasticizer capable of plasticizing the film-forming polymer, wherein the weight fraction of the film-forming polymer in the admixture is greater than the weight fraction of either the complementary multifunctional polymer or the plasticizer.

In a preferred embodiment, the recurring functional groups and the recurring polar groups are ionogenic, and an ionizing agent is incorporated into the admixture so as to ionize up to approximate 30% of the ionogenic groups.

In another embodiment, a water-insoluble, water-absorbent adhesive composition is provided which comprises a blend of:

(a) a film-forming, hydrophilic polymer comprising at least one linear segment containing a plurality of recurring polar groups;

(b) a complementary multifunctional polymer containing a plurality of recurring functional groups along the polymer backbone, said recurring functional groups capable of non-covalently binding to the recurring polar groups so that a ladder-like interpolymer complex is formed between the at least one linear segment and the complementary multifunctional polymer; and (c) a plasticizer capable of plasticizing the film-forming polymer, wherein the weight fraction of the film-forming polymer in the blend is greater than the weight fraction of either the complementary multifunctional polymer or the plasticizer.

DETAILED DESCRIPTION OF THE INVENTION

Definitions and Overview

Figure 1:
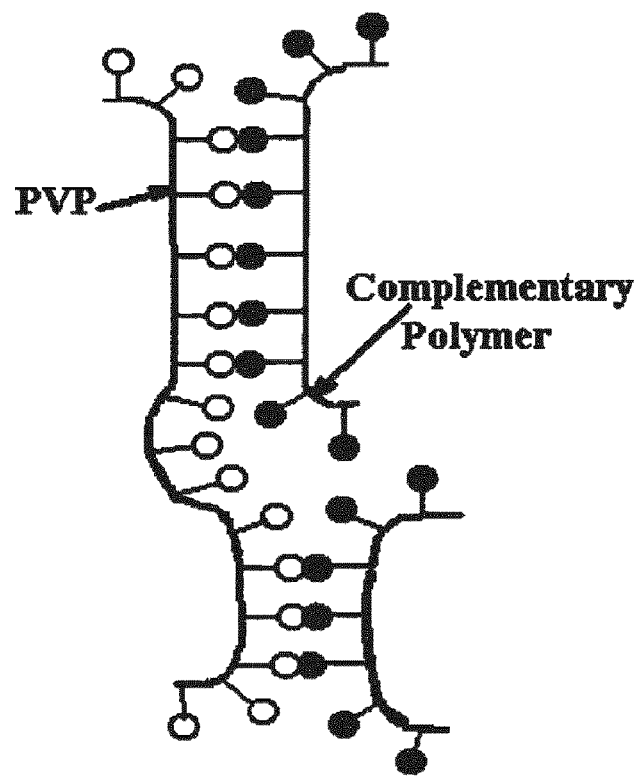
FIG. 1 is a schematic representation of a "ladder-like" interpolymer complex formed by noncovalent association of PVP and a complementary multifunctional polymer containing a plurality of recurring proton-donating functional groups along the polymer backbone, wherein the noncovalent association involves hydrogen bonding between the proton-donating functional groups and the oxo moieties within the pyrrolidone rings. While the formation of a "carcass-like" complex (described infra and illustrated in FIG. 2) leads to enhanced cohesive strength and free volume, the formation of a ladder-like complex as illustrated in this figure is accompanied by a decrease in solubility, an increase in cohesive strength), and a decrease in free volume. For this reason, a polymer blend composed of a ladder-like interpolymer complex provides no adhesion.

It is to be understood that, unless otherwise indicated, this invention is not limited to specific polymers, oligomers, crosslinking agents, additives, manufacturing processes, or adhesive products. It is also to be understood that the terminology used herein is for the purpose of describing particular embodiments only, and is not intended to be limiting.

In describing and claiming the present invention, the following terminology will be used in accordance with the definitions set out below.

The singular forms "a," "an," and "the" include plural referents unless the context clearly dictates otherwise. Thus, for example, reference to "a hydrophilic polymer" includes not only a single hydrophilic polymer but also two or more hydrophilic polymers that mayor may not be combined in a single composition, reference to "a plasticizer" includes a single plasticizer as well as two or more plasticizers that may or may not be combined in a single composition, and the like.

A "hydrophobic" polymer absorbs only up to 1 wt. % water at 100% rh, while "hydrophilic" polymers absorb at least 1 wt. % water at 100% rh.

A "water-swellable" polymer is one that is capable of absorbing water in an amount that is at least 50% of its own weight. That is, a water-swellable polymer weighing×grams can absorb at least 0.5× grams of water, to provide a hydrated polymer weighing at least 1.5× grams and having a polymer to water (weight) ratio of at most 3:1.

The term "crosslinked" herein refers to a polymer composition containing intramolecular and/or intermolecular non covalent bonds. Noncovalent bonding includes hydrogen bonding, electrostatic bonding, and ionic bonding.

The term "polymer" as used herein includes both linear and branched polymers, and homopolymers as well as copolymers, the latter including all types of copolymer structures (e.g., block copolymers, alternating copolymers, random copolymers, etc.) as well as "higher order" copolymers e.g., terpolymers). Those compounds referred to herein as "oligomers" are polymers having a molecular weight below about 1000 Da, preferably below about 800 Da.

The term "water-insoluble" is used to refer to a polymer, compound or composition whose aqueous solubility measured at 20° C. is less than 5 wt %, preferably less than 3 wt %, and more preferably less than 1 wt %. The term "insoluble" is used to refer to a polymer, compound or composition whose solubility in water, polar organic solvents, and possibly nonpolar organic solvents, measured at 20° C., is less than 5 wt %, preferably less than 3 wt %, and more preferably less than 1 wt %.

The term "hydrogel" is used in the conventional sense to refer to water-swellable polymeric matrices that can absorb a substantial amount of water to form elastic gels, where the "matrices" are three-dimensional networks of macromolecules held together by covalent or non-covalent crosslinks. Upon placement in an aqueous environment, dry hydrogels swell to the extent allowed by the degree of cross-linking.

The term "hydrogel composition" refers to a composition that either contains a hydrogel or is entirely composed of a hydrogel. As such, "hydrogel compositions" encompass not only hydrogels per se but also compositions that comprise a hydrogel and one or more non hydrogel components or compositions, e.g., hydrocolloids, which contain a hydrophilic component (which may contain or be a hydrogel) distributed in a hydrophobic phase.

The terms "tack" and "tacky" are qualitative. However, the terms "substantially nontacky," "slightly tacky," and "tacky," as used herein, may be quantified using the values obtained in a PKI tack determination, a TRBT tack determination, or a PSA tack determination/Polyken Probe (Solutia, Inc.). The term "substantially nontacky" is used to refer to a composition having a tack value less than about 25 g-cm/sec, the term "slightly tacky" refers to a composition having a tack value in the range of about 25 g-cm/sec to about 100 g-cm/sec, and the term "tacky" refers to a composition having a tack value of at least 100 g-cm/see.

The term "plasticizer" is used in the conventional sense of the term to refer to a relatively low molecular weight compound that is miscible with a polymer or polymer blend and decreases the glass transition temperature and elastic modulus thereof.

It is desirable to obtain water-insoluble, water-swellable hydrophilic adhesive polymers (adhesive hydrogels) that are capable to form homogeneous films either upon casting a solution to backing layer followed by drying, or under external pressure or by means of extrusion. The film-forming capability requires that the blend has to be free of covalent crosslinks. Blending the polymers provides a convenient way to obtain composite materials with specifically tailored properties, since the properties of the blend are typically intermediate between those of the unblended components when the components are immiscible or partly miscible. In order to make the composite insoluble in water, water-insoluble materials are usually mixed with water-soluble materials. When this is done, however, a phase separation can often occur that does not favor adhesion. Moreover, the insolubility of blend components may hamper the procedure of blend preparation, which often involves the dissolution of all the components in a common solvent, followed by casting the solution and drying.

Preparation of polymer composite materials whose properties are new and untypical of parent components requires a high skill of a material designer. This challenge may be resolved if the blend components are capable of a strong favorable interaction to each other. More often, such interaction is hydrogen, electrostatic or ionic bonding. In this instance mixing of two or more soluble polymers can give their ladder-like complex schematically shown in FIG. 1 that is swellable, but insoluble or partly soluble.

In order to resolve these problems, this invention is directed to a method of obtaining water-insoluble, film-forming compositions by blending soluble polymers, more specifically by blending hydrophilic polymers with complementary macromolecules that are capable of hydrogen bonding, electrostatic or ionic bonding.

By way of overview, the adhesive compositions of the invention contain at least film-forming hydrophilic polymer having at least one linear segment with a plurality of recurring polar groups thereon, at least one complementary multifunctional polymer that serves as a "ladder-like" noncovalent crosslinker of the film-forming polymer, and at least one plasticizer compatible with (i.e., miscible with) or at least partially compatible with both the film-forming polymer and the complementary multifunctional polymer. The film-forming polymer is present in a higher concentration than the complementary multifunctional polymer, and it is this higher concentration that determines the film-forming characteristics. Therefore, while there may be materials that are suitable for use as either the film-forming polymer or as the complementary multifunctional polymer, their function in the composition is determined by the quantity of the component in the composition. If the recurring polar groups or the recurring functional groups are ionogenic, another factor that controls the performance of composite material is the degree of ionization or pH of the mixture.

For example, polyacids such as acrylate polymers bearing carboxyl proton-donating functional groups or polyols bearing hydroxyl proton-donating functional groups and proton-accepting polymers such as poly(N-vinyl lactams) or polyamines are suited for use as both the film-forming polymer or as the complementary multifunctional polymer, in a composition having a greater amount of an acrylate or another proton-donating polymer relative to the amount of a poly(N-vinyl lactam), the acrylate polymer serves as the film-forming polymer and the poly(N-vinyl lactam) or polyamine or another proton-accepting polymer serves as the complementary multifunctional polymer, or ladder-like crosslinker. Similarly, in a composition having a greater amount of a poly(N-vinyl lactam) or polyamine relative to the amount of an acrylate polymer, the poly(N-vinyl lactam) or polyamine serves as the film-forming polymer and the acrylate polymer serves as the ladder-like crosslinker.

Maintaining a specified pH value in the blend or in an admixture used to provide the blend provides an additional factor controlling the performance of the blend when one or more ionogenic polymers are present ionized groups are capable of ionic, but not electrostatic or hydrogen bonding. Fully or partly ionized polymers are always soluble in water, whereas non-ionized polymers as a rule are insoluble or poorly soluble in water. Consequently, the degree of ionization affects appreciably the solubility and swelling of interpolymer complexes involving ionogenic polymers. Moreover, by varying the pH value and degree of ionization, the adhesive properties of composite materials can be controlled. Indeed, adhesion is a result of specific balance between cohesive interaction energy and free volume. As polymeric components bear opposite charges, cohesion is increased. As two polymers have the same positive or negative charge, cohesion is immediately suppressed and free volume is increased. Moreover, due to electrostatic repulsion between the functional groups of identical charge, the chain rigidity and free volume is usually increased. All these factors dramatically affect adhesive performance.

The adhesion profile of the water-insoluble, film-forming compositions of the invention can be tailored based on materials, the ratio of components in the composition, the degree of ionization and the quantity of water in the blend. The ladder-like crosslinker, its ratio to the amount of film-forming polymer, concentration of a plasticizer and ionization degree are selected so as to provide the desired adhesion profile with respect to hydration. Generally, the compositions that are relatively slightly crosslinked through comparatively loose hydrogen bonds and demonstrating a large free volume provide initial tack in dry state. When the degree of cross linking degree and the cohesive strength of the network in the interpolymer complex is above some critical value, the energy of cohesion dominates under free volume and such compositions are usually non-tacky in the dry state. However, as a free volume is increased in this blend (e.g. by adding a suitable plasticizer), adhesion immediately appears. Because water is a good plasticizer for hydrophilic polymers, absorption of the water leads to an improvement of adhesion. Because electrostatic bonds are appreciably stronger than the hydrogen bonds, the cohesion in the blends of polymers bearing carboxyl groups is usually higher than in the materials composed of polymers having hydroxyl groups. Adhesion in such blends appears normally with a higher concentration of absorbed water. Flexible polymers provide higher cohesion than polymers with rigid chains. As an example, for blends of poly(vinyl pyrrolidone) (PVP) as a film-forming polymer, when the ladder-like crosslinker is a rigid-chain cellulose ester bearing OH groups, the composition is generally tacky prior to contact with water (e.g., with a moist surface) but gradually loses tack as the composition absorbs moisture. When the ladder-like crosslinker is an acrylate polymer or copolymer with carboxyl groups, a composition is provided that is generally substantially nontacky prior to contact with water, but that becomes tacky upon contact with a moist surface, Polymer Components:

The film-forming hydrophilic polymer and the complementary multifunctional polymer, as noted elsewhere herein, are generally selected from the same classes of polymers and copolymers, but have complementary groups along the backbone that interact to form noncovalent bonds (e.g., hydrogen bonds, electrostatic bonds, or ionic bonds), thereby forming a ladder-like complex that is insoluble in aqueous liquids, polar organic solvents, and many nonpolar organic solvents as well. By definition herein, the polymer that serves as the "film-forming" polymer represents a greater weight fraction in the mixtures and compositions of the invention that does the complementary multifunctional polymer. Typically, the film-forming hydrophilic polymer represents approximately 20 wt. % to approximately 95 wt. % of the mixtures and compositions of the invention, while the complementary multifunctional polymer represents approximately 0.5 wt. % to approximately 40 wt. % of the mixtures and compositions or the invention. Generally, although not necessarily, the film-forming polymer will also have a higher molecular weight than the complementary multifunctional polymer. The molecular weight of the film-forming polymer will usually be in the range of about 20,000 to 3,000,000, preferably in the range of about 100,000 to 2,000,000, and most preferably in the range of about 100,000 to 1,500,000.

The recurring polar groups on the film-forming polymer and the recurring functional groups on the complementary multifunctional polymer may comprise backbone heteroatoms, e.g., an oxygen atom in an ether (—O—) or ester (—(CO)—O—) linkage, a nitrogen atom in an amine (—NH—), imine (—N=), or amide (—NH(CO)—) linkage, a sulfur atom in a thioether (—S—) linkage, and the like. The recurring polar groups and the recurring functional groups may also comprise pendant groups, for instance:

hydroxyl;
sulfhydryl;
$C_1$-$C_{18}$ hydrocarbyloxy, preferably $C_1$-$C_8$ alkoxy;
$C_2$-$C_{18}$ acyl, preferably $C_2$-$C_8$ acyl (e.g. $C_2$-$C_8$ alkylcarbonyl);
$C_2$-$C_{18}$ acyloxy, preferably $C_2$-$C_8$ acyloxy (e.g., $C_2$-$C_8$ alkylcarbonyloxy);
$C_2$-$C_{18}$ hydrocarbyloxy carbonyl (—(C0)-0-alkyl), preferably $C_2$-$C_8$ alkoxycarbonyl (—(CO)—O-alkyl));
carboxy (—COOH),
carboxylato (—COO$^-$);
carbamoyl (—(C0)-NR$_2$ wherein R is H or $C_1$-$C_{18}$ hydrocarbyl, preferably H or $C_1$-$C_8$ alkyl);
cyano(—C≡N);
isocyano (—N$^+$≡C$^-$);
cyanato (—O—C≡N);
isocyanato (—O—N$^+$≡C$^-$);
formyl (—(CO)—H);
amino, i.e., —NR$^1$R$^2$ where R$^1$ and R$^2$ are independently selected from H and $C_1$-$C_{18}$ hydrocarbyl, preferably selected from H, $C_1$-$C_8$ alkyl, and $C_5$-$C_{12}$ aryl, or are linked to form an optionally substituted five- or six-membered ring, thus including mono-($C_1$-$C_8$ alkyl)-substituted amino, di-($C_1$-$C_8$ alkyl)-substituted amino, mono-($C_5$-$C_{17}$ aryl)-substituted amino, and di-($C_5$-$C_{12}$ aryl)-substituted amino), piperidinyl, pyrrolidinyl, and pyrrolidonyl;
quaternary ammonium, i.e., —[NR$^3$R$^4$R$^5$]$^+$Q$^-$ where R$^3$, R$^4$, and R$^5$ are $C_1$-$C_{18}$ hydrocarbyl, preferably $C_1$-$C_8$ alkyl, and most preferably $C_1$-$C_4$ alkyl, and Q is a negatively charged counterion, e.g., a halogen anion;
$C_2$-$C_{18}$ alkylamido, preferably $C_2$-$C_8$ alkylamido (—NH—(CO)-alkyl);
$C_6$-$Q_{18}$ arylamido, preferably $C_6$-$C_{12}$ alkylamido (—NH—(CO)-aryl);
nitro (—NO$_2$);
sulfo (—SO$_2$—OH);
sulfonato (—SO$_2$—O$^-$);
$C_1$-$C_{18}$ hydrocarbylsulfanyl, preferably $C_1$-$C_8$ alkysulfanyl (—S-hydrocarbyl and —S-alkyl, respectively, also termed "hydrocarbylthio" and "alkylthio");
phosphono (—P)(O)(OH)$_2$);
phosphonato (—P(O)(O$^-$)$_2$);
phosphinato (—P(O)(O$^-$)); and
phospho (—PO$_2$), any of which may be substituted as permitted, e.g., with hydrocarbyl groups and/or additional functional groups. The pendant groups may also be directly linked to an atom in the polymer backbone, or they may be indirectly linked through a linking group (e.g., $C_1$-$C_{18}$ hydrocarbylene linker such as $C_2$-$C_8$ alkylene linker). Additionally, there may be two or more types of polar groups on the film-forming polymer (which may include backbone heteroatoms as well as pendant polar groups) and two or more types of functional groups on the complementary multifunctional polymer (again, which may include backbone heteroatoms as well as pendant polar groups).

Preferred pendant groups are those present on polymers that are readily synthesized or commercially available, typically including hydroxy. $C_1$-$C_8$ alkoxy, carboxyl, carboxylato, sulfo, sulfonato, amino, di($C_1$-$C_8$ alkyl)-substituted amino, quaternary ammonium, piperidinyl, pyrrolidinyl, pyrrolidinyl, and phosphono groups.

In general, it is also preferred, although not essential, that the film-forming polymer have an excess of polar groups relative to the corresponding functional groups on the complementary multifunctional polymer, such that, providing that the polar groups and functional groups are ionogenic, the ladder-like complex can readily ionized in the presence of an ionizing agent, e.g., an acid or base. Typically, zero to about 30% of the ionogenic groups present on the film-forming polymer are ionized, preferably about 5% to 10%. The degree of ionization may be controlled by addition of a suitable ionizing agent, e.g., an acid or base.

It will be appreciated by those of ordinary skill in the art that virtually any polymers meeting the aforementioned criteria may be used herein. Suitable polymers include, but are not limited, to the following:

poly(N-vinyl lactams) such as poly(vinyl pyrrolidone), poly(vinyl-2-valerolactam), and poly(N-vinyl-2-caprolactam);

polyvinyl alcohols, including polyvinyl alcohol per se and polyvinyl phenol;

polyacrylamides such as poly(N-methacrylamide), poly(N,N-dimethylacrylamide), poly(N-isopropylacrylamide) (PNIPAM), poly(N-vinyl acrylamide), and other poly(N-alkyl acrylamides and N-alkenyl acrylamides);

poly(alkylene oxides) such as polyethylene oxide (PEO) and poloxamers copolymers of ethylene oxide and propylene oxide);

poly(oxyethylated) alcohols such as poly(oxyethylated) glycerol, poly(oxyethylated) sorbitol, and poly(oxyethylated) glucose;

polylactide and poly(lactide-co-glycolide);

poly(acrylic acid), poly(methacrylic acid), poly(maleic acid), poly(fumaric acid), alginic acid, and poly(sulfonic acids);

polyvinyl amines);

poly(alkylene imines);

cellulose esters and other cellulose derivatives, including carboxymethylcellulose, cellulose acetate, cellulose acetate butyrate, cellulose acetate propionate, cellulose butyrate, cellulose diacetate, cellulose phthalate, cellulose propionate, cellulose propionate butyrate, cellulose triacetate, hydroxyethylcellulose, hydroxypropylcellulose, hydroxypropyl methylcellulose, hydroxypropylmethylcellulose phthalate, methylcellulose, sodium carboxymethylcellulose; and acrylate and methacrylate polymers and copolymers, including poly(dialkyl aminoalkyl acrylates), poly(dialkyl aminoalkyl methacrylates), poly(hydroxyalkyl acrylates) such as poly(hydroxyethyl acrylate), and poly(hydroxyalkyl methacrylates) such as poly(hydroxyethyl methacrylate) (PolyHEMA). Preferred acrylate polymers are those copolymers available under the tradename "Eudragit" from Rohm Pharma (Germany). The Eudragit series E, F, S, RL, RS, and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit E-30D-55 and Eudragit L-100-55 (the latter copolymer is a spray-dried form of Eudragit L-30D-55 that can be reconstituted with water). The molecular weight of the Eudragit L-30D-55 and Eudragit L-100-55 copolymer is approximately 135,000 Da, with a ratio of free carboxyl groups to ester groups of approximately 1:1. The copolymer is generally insoluble in aqueous fluids having a pH below 5.5. Another particularly suitable methacrylic acid-methyl methacrylate copolymer is Eudragit S-100, which differs from Eudragit L-30D-55 in that the ratio of free carboxyl groups to ester groups is approximately 1:2. Eudragit S-100 is insoluble at pH below 5.5, but unlike Eudragit L-30D-55, is poorly soluble in aqueous fluids having a pH in the range of 5.5 to 7.0. This copolymer is soluble at pH 7.0 and above. Eudragit L-100 may also be used, which has a pH-dependent solubility profile between that of Eudragit L-30D-55 and Eudragit S-100, insofar as it is insoluble at a pH below 6.0. It will be appreciated by those skilled in the art that Eudragit L-30D-55, L-100-55, L-100, and S-100 can be replaced with other acceptable polymers having similar pH-dependent solubility characteristics. Other preferred Eudragit polymers are cationic, such as the Eudragit E, RS, and RL series polymers. Eudragit E100 and E PO are cationic copolymers of dimethylaminoethyl methacrylate and neutral methacrylates (e.g., methyl methacrylate), while Eudragit RS and Eudragit RL polymers are analogous polymers, composed of neutral methacrylic acid esters and a small proportion of trimethylammonioethyl methacrylate.

Copolymers of any of the above may also be used herein, as will be appreciated by those of ordinary skill in the art.
Plasticizers:

Suitable plasticizers and softeners include, by way of illustration and riot limitation: alkyl and aryl phosphates such as tributyl phosphate, trioctyl phosphate, tricresyl phosphate, and triphenyl phosphate; alkyl citrates and citrate esters such as trimethyl citrate, triethyl citrate and acetyl triethyl citrate, tributyl citrate and acetyl tributyl citrate, acetyl triethyl citrate, and trihexyl citrate; alkyl glycerolates; alkyl glycolates; dialkyl adipates such as dioctyl adipate (DOA; also referred to as bis(2-ethylhexyl)adipate), diethyl adipate, di(2-methylethyl)adipate, and dihexyl adipate; dialkyl phthalates, dicycloalkyl phthalates, diaryl phthalates and mixed alkyl-aryl phthalates, including phthalic acid esters, as represented by dimethyl phthalate, diethyl phthalate, dipropyl phthalate, dibutyl phthalate, di(2-ethylhexyl)-phthalate, di-isopropyl phthalate, diamyl phthalate and dicapryl phthalate; dialkyl sebacates such as diethyl sebacate, dipropyl sebacate, dibutyl sebacate and dinonyl sebacate; dialkyl succinates such as diethyl succinate and dibutyl succinate; dialkyl tartrates such as diethyl tartrate and dibutyl tartrate; glycol esters and glycerol esters such as glycerol diacetate, glycerol triacetate (triacetin), glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; hydrophilic surfactants, preferably hydrophilic non-ionic surfactants such as, for example, partial fatty acid esters of sugars, polyethylene glycol fatty acid esters, polyethylene glycol fatty alcohol ethers, and polyethylene glycol sorbitan-fatty acid esters, as well as non-ionic surfactants such as ethylcellosolve; lower alcohols from ethyl to octyl; sorbitol; tartaric acid esters such as dibutyl tartrate; and mixtures thereof.

A preferred plasticizer for use in conjunction with the present invention is a bifunctional oligomer that is "complementary" to the film-forming polymer as described in U.S. Pat. No. 6,576,712 to Feldstein et al., cited earlier herein. Preferably, the complementary oligomer is terminated with hydroxyl groups, amino or carboxyl groups. The oligomer typically has a glass transition temperature $T_g$ in the range of about $-100°$ C. to about $-30°$ C. and a melting temperature $T_m$ lower than about 20° C. The oligomer may be also amorphous. The difference between the $T_g$ value of the film-forming polymer and that of the complementary oligomer is preferably greater than about 50° C., more preferably greater than about 100° C., and most preferably in the range of about 150° C. to about 300° C., Generally, the oligomer will have a molecular weight in the range from about 45 to about 800, preferably in the range of about 45 to about 600. Examples of suitable oligomers include, but are not limited to, low molecular weight polyalcohols (e.g. glycerol), oligoalkylene glycols such as ethylene glycol and propylene glycol, ether alcohols (e.g., glycol ethers), alkane diols from butane diol to octane diol, including carboxyl-terminated and amino-terminated derivatives of polyalkylene glycols. Polyalkylene glycols, optionally carboxyl-terminated, are preferred herein, and polyethylene glycol having a molecular weight in the range of about 300 to 600 is an optimal complementary oligomer.

The compositions of the invention may also include two or more plasticizers in combination, e.g., triethyl citrate and tributyl citrate, triethyl citrate and polyethylene glycol 400, polyethylene glycol 400 and dioctyl phthalate, etc.
Representative Compositions:

An illustrative composition includes poly(N-vinyl-2-pyrrolidone) ("PVP") as the film-forming polymer and polyethylene glycol ("PEG") as the carcass-like non-covalent crosslinker. Mixing a PVP-PEG adhesive blend with a ladder-like non-covalent crosslinker that is a moderately hydrophilic or water-insoluble polymer results in the decrease of blend hydrophilicity and dissolution rate. In order to decrease the dissolution rate further or to obtain insoluble mixtures, the PVP-PEG blend can be mixed with polymers that bear complementary (with respect to PVP) reactive functional groups in their repeating units. Since the PVP contains proton-accepting carbonyl groups in its repeating units, the complementary functional groups are preferably proton-donating, hydroxyl or carboxyl groups. Thus, for use with PVP and PEG, suitable ladder-like non-covalent crosslinkers are long chain polymers such as polyvinyl alcohols, polyacrylic acids, polymethacrylic acids, homo- and co-polymers thereof, as well as sulfonic acid and alginic acid.

Another illustrative composition uses a copolymer of methacrylic acid and methyl methacrylate as the ladder-like non-covalent crosslinker with the PVP/PEG noted above. This composition is used to facilitate in understanding the principles of the invention.

Figure 2:
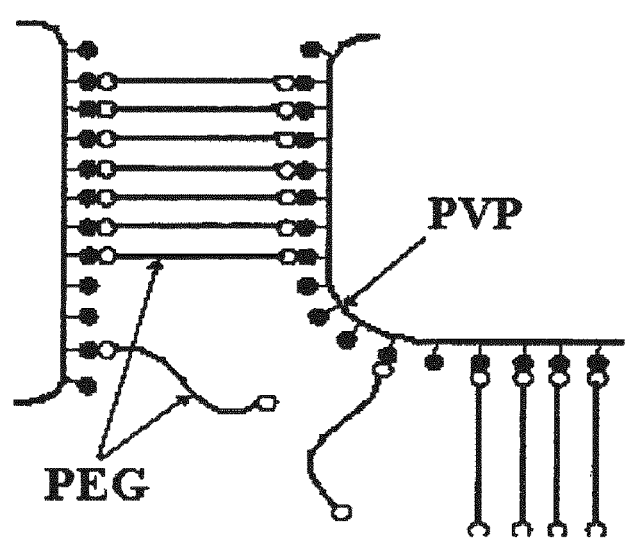
FIG. 2 is a schematic representation of a "carcass-like" complex formed by noncovalent association of PVP and oligomeric PEG, wherein the bifunctional oligomer provides a bridge between two polymer chains and the noncovalent association involves hydrogen bonding; between terminal proton-donating moieties on the PEG and the oxo moieties within the pyrrolidone rings. The complex combines high cohesive toughness (as a result of the hydrogen bonding) with a large free volume resulting from the length and flexibility of the PEG chains).

The PVP-PEG complex combines high cohesive toughness (due to PVP-PEG H-bonding) with a large free volume (resulting from considerable length and flexibility of PEG chains). In order to emphasize enhanced free volume in the PVP-PEG blend, this type of complex structure is defined as a "carcass-like" structure (see FIG. 1). The carcass-like structure of the complex, results from the location of reactive functional groups at both ends of PEG short chains. When the ladder-like non-covalent crosslinker contains reactive functional groups in repeating units of the backbone, the resulting complex has so-called "ladder-like" structure (see FIG. 2). The ladder-like type of interpolymeric complex was first described by Kabanov et al. (1979) *Vysokomol. Soed.* 21(A): 243-281). While the formation of the carcass-like complex leads to enhanced cohesive strength and free volume (which determines the adhesive properties of PVP-PEG blends), the formation of the ladder-like complex shown in FIG. 2 is accompanied by the loss of blend solubility and the increase of cohesive strength coupled with the decrease in free volume. For this reason, the structure of the ladder-like complex provides no adhesion.

Due to the decrease in free volume and the increase in cohesive energy, the PVP-PEG blend mixed with a long chain polymer giving the ladder-like complex with PVP, provides no or negligible initial tack. However, as the non-adhesive PVP-PEG blend with the long chain polymer is plasticized by water, the glass transition temperature of the blend shifts toward lower values, which are typical features of pressure-sensitive adhesives, and adhesion arises.

There are certain preferred combinations of components in the adhesive composition. For example, when the film-forming polymer is a poly(N-vinyl lactam) such as poly(N-vinyl pyrrolidone) or poly(N-vinyl caprolactam), the ladder-like crosslinker is preferably a poly(dialkyl aminoalkyl acrylate), poly(dialkyl aminoalkyl methacrylate), polyacrylic acid, polymethacrylic acid, polyvinyl alcohol, poly(hydroxyalkyl acrylate), or poly(hydroxyalkyl methacrylate) such as poly (hydroxyethyl methacrylate).

Similarly, when the film-forming polymer is a poly(dialkyl aminoalkyl acrylate), poly(dialkyl aminoalkyl methacrylate), polyacrylic acid, polymethacrylic acid, polymaleic acid, polyvinyl alcohol, polyvinyl phenol, or poly(hydroxyalkyl acrylate) such as poly(hydroxyethyl methacrylate), the ladder-like crosslinker is preferably a poly(dialkyl aminoalkyl acrylate, poly(dialkyl aminoalkyl methacrylate), poly(N-vinyl lactam) such as poly(N-vinyl pyrrolidone) or poly(N-vinyl caprolactam), as well as a copolymer of poly(N-dialkylamino alkyl acrylate) with alkyl acrylate, polyethylene oxide, methacrylate or ethylacrylate monomers, or a copolymer poly(N-dialkylamino alkyl methacrylate) and alkyl acrylate, methacrylate or ethacrylate monomers.

For any of the aforementioned combinations, a preferred carcass-like crosslinker is an oligomeric alkylene glycol comprising about 1-20 alkylene oxide units in its chain such as polyethylene glycol, carboxyl-terminated oligomeric alkylene glycol such as carboxyl-terminated poly(ethylene glycol), or polyhydric alcohols.

Other examples of suitable blends are shown in following table:

| film-forming polymer | ladder-like crosslinker | carcass-like crosslinker |
|---|---|---|
| PVCap | Eudragit L 100, PAA, PMA, PVA, polyvinyl phenol and PolyHEMA | PEG and carboxyl terminated PEG |
| PNIPAM | Eudragit L 100, L 100-55, S-100, PAA, PMA, alginic acid, PVA, and PolyHEMA | PEG and carboxyl terminated PEG |
| PEO | Eudragit L 100, L 100-55, S-100, PAA, PMA, alginic acid, GANTREZ ES-225, GANTREZ ES-425, polyvinyl phenol | Propylene glycol, Glycerol, PEG, PEG-diacid |
| PAA, PMA | Eudragit E-100* and polyvinyl amine | PEG |
| Eudragit E-100* | PAA, PMA, Eudragit L 100, L 100-55, S 100 and alginic acid | Carboxyl terminated PEG, carbonic di- and polyvalent acids** |

*Eudragit E-100 is a copolymer of 2-dimethylaminoethyl methacrylate, butyl methacrylate and methyl methacrylate 2:1:1, commercially available from Rohm Pharma Polymers
**As described in U.S. Pat. No. 6,576,712

To illustrate the approach used herein, a PVP-PEG-Eudragit blend was used as a typical example, although the approach is general and can be easily reproduced using other water-soluble, hydrophilic polymers.

The properties of adhesive polymer blends were evaluated and are set forth in the examples. The behavior of these polymer blends was found to be typical of covalently crosslinked polymers. However, in contrast to covalently crosslinked systems, the triple polymer blends combining the carcass-like and the ladder-like non-covalent crosslinkers can be easily prepared using a straightforward process, and, furthermore, provide film-forming properties that are unattainable using chemically crosslinked polymers.

Additives:

The adhesive compositions of the invention may also include one or more conventional additive, which may be combined with the polymers and the plasticizer during adhesive formulation or incorporated thereafter. Optional additives include, without limitation, fillers, pH regulating agents, ionizing agents, tackifiers, detackifying agents, electrolytes, antimicrobial agents, antioxidants, preservatives, colorants, flavors, and combinations thereof.

In certain embodiments, the compositions of the invention may also include a pharmacologically active agent or a cosmeceutically active agent. For instance, transdermal, transmucosal, and topical delivery systems in which an adhesive composition of the invention serves as a drug reservoir and/or skin contact adhesive layer may be formulated for the delivery of a specific pharmacologically active agent. Cosmeceutical products such as tooth whitening gels and strips may be formulated for the delivery of one or more tooth-whitening agents. Examples of such products are described in pending U.S. patent application Ser. No. 10/936,887 to Feldstein et al. for "Method of Preparing Polymeric Adhesive Compositions Utilizing the Mechanism of Interaction Between The Polymer Components, filed Sep. 8, 2004, and U.S. Patent Application Ser. No. 60/638,835 to Singh et al. for "Sustained Release Tooth Whitening Systems and Formulations," filed Dec. 21, 2004, the disclosures of which are incorporated by reference herein.

Absorbent fillers may be advantageously incorporated to control the degree of hydration when the adhesive is on the skin or other body surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, woven and nonwoven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon. A preferred filler is colloidal silica, e.g., Cab-O-Sil® (Cabot Corporation, Boston Mass.).

Compounds useful as pH regulators include, but are not limited to, glycerol buffers, citrate buffers, borate buffers, phosphate buffers, and citric acid-phosphate buffers. Buffer systems are useful to ensure, for instance, that the pH of a composition of the invention is compatible with that of an individual's body surface.

Ionizing agents are also useful to impart a desired degree of ionization to the interpolymer complex within the adhesive compositions of the invention. Suitable ionizing agents are acids and bases, depending on the group to be ionized. The acids and bases may be inorganic (hydrochloric acid, hydrobromic acid, sodium hydroxide, potassium hydroxide, sodium carbonate, ammonium carbonate, etc.) or organic (acetic acid, maleic acid, triethylamine, ethanolamine, etc.).

Tackifiers can also be included to improve the adhesive and tack properties of the compositions of the invention. The mechanism underlying tack improvement results from the large size and hydrophobic character of tackifier molecules. Exemplary tackifying materials include tacky rubbers such as polyisobutylene, polybutadiene, butyl rubber, polystyrene-isoprene copolymers, polystyrene-butadiene copolymers, and neoprene (polychloroprene). Other examples of suitable tackifiers herein are those that are conventionally used with pressure sensitive adhesives, e.g., rosins, rosin esters, polyterpenes, and hydrogenated aromatic resins. In those embodiments wherein adhesion is to be reduced or eliminated, conventional detackifying agents may also be used. Suitable detackifiers include crosslinked poly(vinylpyrrolidone), silica gel, bentonites, and so forth.

Preferred thickeners herein are naturally occurring compounds or derivatives thereof, and include, by way of example: collagen; galactomannans; starches; starch derivatives and hydrolysates; cellulose derivatives such as methyl cellulose, hydroxypropylcellulose, hydroxyethyl cellulose, and hydroxypropyl methyl cellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

The compositions of the invention can be rendered electrically conductive for use in biomedical electrodes and other electrotherapy contexts, i.e., to attach an electrode or other electrically conductive member to the body surface. For example, the composition may be used to attach a transcutaneous nerve stimulation electrode, an electrosurgical return electrode, or an EKG electrode to a patient's skin or mucosal tissue. These applications involve modification of the composition so as to contain a conductive species. Suitable conductive species are ionically conductive electrolytes, particularly those that are normally used in the manufacture of conductive adhesives used for application to the skin or other body surface, and include ionizable inorganic salts, organic compounds, or combinations of both. Examples of ionically conductive electrolytes include, but are not limited to, ammonium sulfate, ammonium acetate, monoethanolamine acetate, diethanolamine acetate, sodium lactate, sodium citrate, magnesium acetate, magnesium sulfate, sodium acetate, calcium chloride, magnesium chloride, calcium sulfate, lithium chloride, lithium perchlorate, sodium citrate and potassium chloride, and redox couples such as a mixture of ferric and ferrous salts such as sulfates and gluconates. Preferred salts are potassium chloride, sodium chloride, magnesium sulfate, and magnesium acetate, and potassium chloride is most preferred for EKG applications. Although virtually any amount of electrolyte may be present in the adhesive compositions of the invention, it is preferable that any electrolyte present be at a concentration in the range of about 0.1 to about 15 wt. % of the hydrogel composition. The procedure described in U.S. Pat. No. 5,846,558 to Nielsen et al. for fabricating biomedical electrodes may be adapted for use with the hydrogel compositions of the invention, and the disclosure of that patent is incorporated by reference with respect to manufacturing details. Other suitable fabrication procedures may be used as well, as will be appreciated by those skilled in the art.

Antimicrobial agents may also be added to the compositions of the invention. Antimicrobial agents function by destroying microbes, preventing their pathogenic action, and/or inhibiting their growth. Desirable properties of antimicrobial agents include, but are not limited to: (1) the ability to inactivate bacteria, viruses and fungi, (2) the ability to be effective within minutes of application and long after initial application, (3) cost, (4) compatibility with other components of composition, (5) stability at ambient temperature, and (6) lack of toxicity.

Antioxidants may be incorporated into the compositions of the invention in lieu of or in addition to any antimicrobial agent(s). Antioxidants are agents that inhibit oxidation and thus prevent the deterioration of preparations by oxidation. Suitable antioxidants include, by way of example and without limitation, ascorbic acid, ascorbyl palmitate, butylated hydroxyanisole, butylated hydroxytoluene, hypophophorous acid, monothioglycerol, sodium ascorbate, sodium formaldehyde sulfoxylate and sodium metabisulfite and others known to those of ordinary skill in the art. Other suitable antioxidants include, for example, vitamin C, butylated hydroxytoluene (BHT), butylated hydroxyanisole (BHA), sodium bisulfite, vitamin E and its derivatives, propyl gallate, sulfite derivatives, and others known to those of ordinary skill in the art.

Other preservatives that can be incorporated into the present compositions include, by way of example, p-chlorom-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

It will be appreciated that because the adhesive compositions of the invention are useful in a variety of contexts, the desirability or need for certain additives may differ depending on the intended use. The applications in which the adhesive compositions of the invention are useful include, for example: drug delivery systems; wound dressings; conductive hydrogels; pressure-relieving cushions for application to the skin including heel cushions, elbow pads, knee pads, shin pads, forearm pads, wrist pads, finger pads, corn pads, callus pads, blister pads, bunion pads, and toe pads, all of which can include active agents; intraoral applications such as tooth whitening strips, breath freshening films, and oral care products to treat sore throat, sores within the mouth, gingivitis, periodontal and oral infections, periodontal lesions, or dental caries or decay; adhesives for affixing medical devices, diagnostic systems and other devices to a body surface; sealants for ostomy devices, prostheses, and face masks; sound, vibration, and impact absorbing materials; carriers in cosmetic and cosmeceutical gel products; and many other uses known to or readily ascertainable by those of ordinary skill in the art, or as yet undiscovered.

Manufacturing Methodologies:

The properties of the compositions of the invention are readily controlled by adjusting one or more parameters during fabrication. For example, the adhesive strength of the composition can be increased, decreased, or eliminated during manufacture, by varying the type and/or quantity of different components, or by changing the mode of manufacture, It should also be noted that compositions prepared using a conventional melt extrusion process generally, although not necessarily, exhibit somewhat different properties relative to compositions prepared using a solution cast technique; for example, melt extrusion is typically more useful for preparing adhesive compositions that having lower tack than corresponding adhesive compositions prepared using solution casting.

The compositions described herein are generally melt extrudable, and thus may be prepared using a simple blending and extruding process. The components of the composition are weighed out and then admixed, for example using a Brabender or Baker Perkins Blender, generally although not necessarily at an elevated temperature, e.g., about 90 to 170° C., typically 100 to 140° C. Solvents or water may be added if desired. The resulting composition can be extruded using a single or twin extruder, or pelletized. Alternatively, the individual components can be melted one at a time, and then mixed prior to extrusion. The composition can be extruded to a desired thickness directly onto a suitable substrate or backing member. The composition can be also extruded first, and then be pressed against a backing member or laminated to a backing member. A releasable liner may also be included. The thickness of the resulting film, for most purposes, will be in the range of about 0.050 to 0.80 mm, more usually in the range of about 0.37 to 0.47 mm.

Alternatively, the compositions may be prepared by solution casting, by admixing the components in a suitable solvent, e.g., a volatile solvent such as ethyl acetate, or lower alkanols (e.g., ethanol, isopropyl alcohol, etc.) are particularly preferred, at a concentration typically in the range of about 35 to 60% w/v. The solution is cast onto a substrate, backing member or releasable liner, as above. Both admixture and casting are preferably carried out at ambient temperature. The material coated with the film is then baked at a temperature in the range of about 80 to 100° C., optimally about 90° C., for time period in the range of about one to four hours, optimally about two hours.

In selecting the components for incorporation into an adhesive composition of the invention, the film-forming hydrophilic polymer is selected first. Then, a complementary multifunctional polymer, with recurring functional groups capable of noncovalent bonding to the recurring polar groups within at least one linear segment of the hydrophilic polymer is selected. The complementary multifunctional polymer serves as a "ladder-like" noncovalent crosslinker that noncovalent bonding to the film-forming polymer results in the formation of a ladder-like interpolymer complex. The plasticizer is then selected, which, as noted elsewhere herein, is a bifunctional linear oligomer capable of forming a bridge between a polar group on one film-forming polymer chain and a polar group on a second film-forming polymer chain, thereby forming a "carcass-like" crosslinked complex. The amount of the film-forming polymer is greater than the amount of the complementary multifunctional polymer and is also greater than the amount of the bifunctional linear oligomer.

Optional additives, including pharmacologically active agents and cosmeceutical agents, can be combined with the polymers and oligomer during adhesive preparation. Alternately, an additive can be added after the components are mixed and the composite on prepared. One method of loading the composition with an active agent, for example, involves providing a layer of the composition on a substrate, coating the layer with a solution of the active agent, placing a release liner on top of the active agent layer, and allowing the active agent to become absorbed by the composition, Experimental:

The following examples are put forth so as to provide those of ordinary skill in the art with a complete disclosure and description of how to manufacture the adhesive compositions of the invention and are not intended to limit the scope of that which the inventors regard as the invention. Efforts have been made to ensure accuracy with respect to numbers (e.g., amounts, temperatures, etc.) but some errors and deviations should be accounted for. Unless indicated otherwise, parts are parts by weight, temperature is in degrees Celsius (° C.), and pressure is at or near atmospheric.

The abbreviations used in the examples are as follows:
AA: adipic acid (Aldrich)
ATBC: acetyltributyl citrate (Rohm America Inc.)
ATEC: acetyltriethyl citrate (Rohm America Inc.)
Cab-O-Sil M5: synthetic silicone dioxide supplied with Cabot Corporation in the form of finely micronized powder.
Carbopol 974; chemically crosslinked polyacrylic acid (Noveon, Inc.)
Eudragit E100: N-dimethylaminoethyl methacrylate copolymer (Rohm America Inc.)
Fadragit L 100-55: methacrylic acid copolymer (Rohm America Inc.)
Eudragit L 100: methacrylic acid copolymer (Rohm America Inc.)
Eudragit S 100; methacrylic acid copolymer (Rohm America Inc.)
Gantrez ES-425: monobutyl ether of maleic acid—methylvinyl ether copolymer (ISP)
Gantrez S-97; maleic acid—methylvinyl ether copolymer (ISP)
HPC: hydroxypropylcellulose
HPMCP: hydroxypropyl methylcellulose phthalate
Kollidon CLM: physically crosslinked polyvinylpyrrolidone supplied with BASF in the form of finely micronized powder.
Oppanol B-15: polyisobutylene (PIB) $M_w$=75,000 g/mol (BASF)
PVP K90: Kollidon® 90F polyvinylpyrrolidone (BASF)
PVP K30; Kollidon® 30F polyvinylpyrrolidone (BASF)
PEG 400: polyethylene glycol 400
Sylvagum RE 85K: glycerol ester of tall oil rosin (Arizona Chemical)
TBC: tributyl citrate (Rohm America Inc.)
TEC: triethyl citrate (Rohm America Inc.)

EXAMPLE 1

Figure 4:
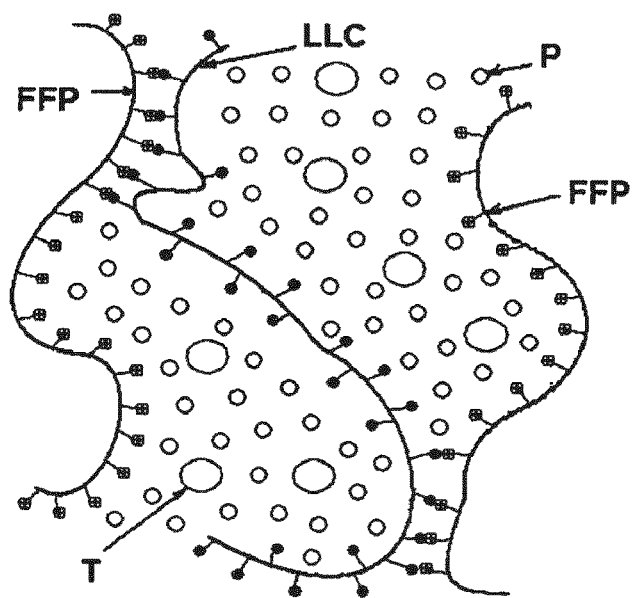
FIG. 4 schematically illustrates the structure of an interpolymer complex composed of a film-forming polymer (FFP) and ladder-like crosslinker (LLC). The complex is mixed with a plasticizer (P) and filled with a tackifier (T).

Preparation and Properties of Adhesive Compositions Based on the Ladder-Like Interpolymer Complexes In the present example, Eudragit E-100 is used as the film-forming polymer, which is a copolymer of 2-dimethylaminoethyl methacrylate (DMAEMA), butyl methacrylate, and methyl methacrylate (2:1:1). The monomer units of DMAEMA are capable of forming electrostatic bonds with carboxyl groups in the ladder-like crosslinker, Eudragit L 100-55 and Eudragit S-100 (copolymer of methacrylic acid with methyl methacrylate (1:2). In this way, these blends represent triple blends of two Eudragit grade polymers (E-100 and L 100-55, or S-100) with appropriate plasticizers of hydrophobic units in Eudragit, such as tributyl citrate (TBC), triethyl citrate (TEC), acetyltributyl citrate (ATBC) and acetyltriethyl citrate (ATEC) (see Scheme in FIG. 4).

| | Blend composition, wt. % | | | | |
|---|---|---|---|---|---|
| Sample | Film-forming polymer: Eudragit E-100 | Ladder-like crosslinker: Eudragit L 100-55 or S-100 | Carcass-like crosslinker | Sol Fraction, % | Swell Ratio |
| 1a | 68 | L 100-55 7 | PEG-400 25 | 25.5 | 2.75 |
| 1b | 68 | L 100-55 7 | TBC 25 | 15.06 | 2.45 |
| 1c | 68 | L 100-55 7 | TEC 25 | 18.62 | 2.64 |
| 1d | 68 | S 100 7 | TEC 25 | 19.67 | 1.15 |
| 1e | 62.5 | L 100-55 12.5 | TEC 25 | 27.86 | 3.31 |
| 1f | 62.5 | S 100 12.5 | TEC 25 | 26.88 | 4.43 |

Preparation of films. Required amounts of TEC, Eudragit E100 and Eudragit L100-55 as indicated in Table Ex-1 were dissolved in ethanol under vigorous stirring. Ethanol/Eudragit E100 weight ratio was 7/3 in all cases. The mixture was stirred over 2 hours to obtain homogeneous solution. The solution was stored over 5 hours to let air bubbles dissipate. Polymer films were prepared by solution casting onto a PET backing with following drying at ambient temperature over 3 days. Films of 0.20±0.04 mm thickness were obtained.

Figure 5:
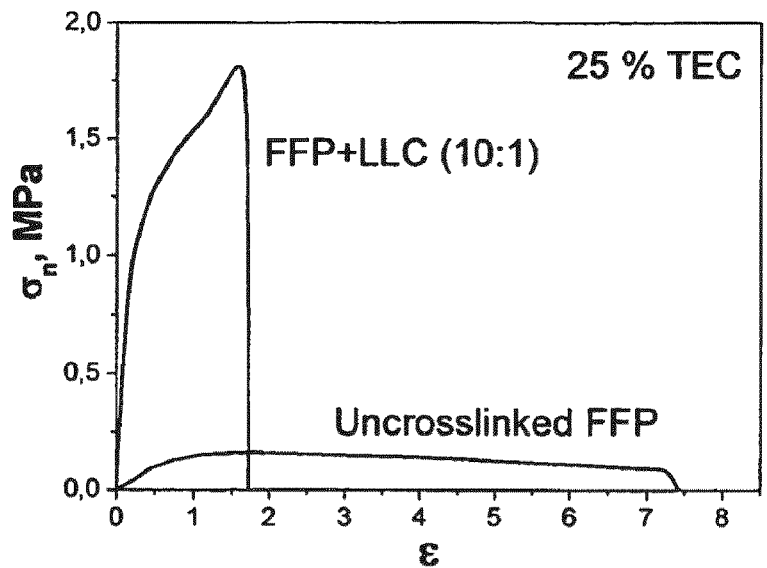
FIG. 5 demonstrates nominal stress-strain curves for uniaxial drawing for the mixture of film-forming Eudragit E-100 polymer with 25 wt. % of TEC and for the ladder-like interpolymer Eudragit E-100-Eudragit L-100-55 complex ([FFP]:[LLC]=10:1) plasticized with the same amount of TEC. Drawing rate is 20 mm/min.
Figure 6:
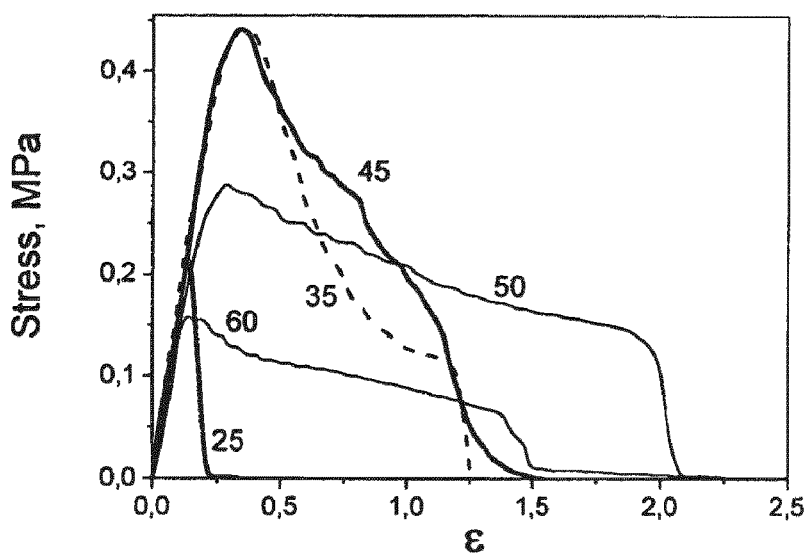
FIG. 6 shows the impact of plasticizer (TEC) concentration on probe tack stress-strain curves of the blends of Eudragit E-100 film forming copolymer and Eudragit L-100-55 ladder-like crosslinker (10:1). The TEC concentrations are indicated in the Figure.
Figure 7:
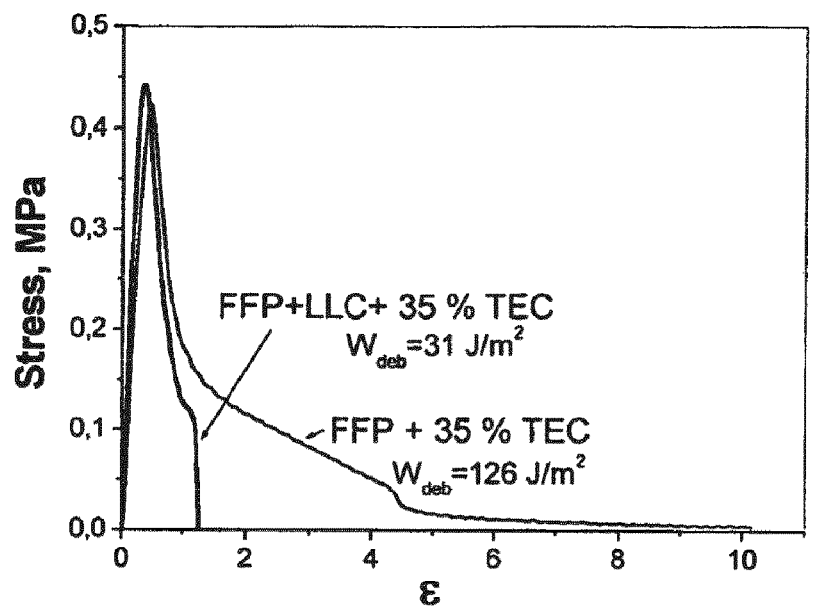
FIG. 7 exhibits the effect of ladder-like electrostatic cross linking of film-forming polybase (Eudragit E-100) by polyacid (Eudragit L-100-55) on probe tack stress-strain curves.

Mechanical and adhesive properties of the Eudragit E100/Eudragit L100-55/TEC films were tested with Tensile and Probe Tack Tests as indicated above. The values of maximum stress and maximum work of adhesive debonding for the tested films are documented in the Table Ex-1, whereas relevant tensile test and probe tack stress-strain curves are presented in FIG. 5-7.

TABLE EXAMPLE 1

| | Composition | | | | |
|---|---|---|---|---|---|
| | Eudragit E-100, grams | Eudragit L 100-55, grams | TEC, grams | $W_{debonding}$ J/m$^2$ | Maximum stress, MPa |
| Ex 1-1 | 68.2 | 6.8 | 25 | 3 | 0.24 |
| Ex 1-2 | 59.1 | 5.9 | 35 | 31 | 0.44 |
| Ex 1-3 | 50 | 5 | 45 | 40 | 0.44 |
| Ex 1-4 | 45.5 | 4.5 | 50 | 41 | 0.29 |
| Ex 1-5 | 36.4 | 3.6 | 60 | 22 | 0.16 |

Pressure sensitive adhesives based on Eudragit E-100-Eudragit L-100-55 blends with plasticizer were first described in U.S. Pat. No. 6,063,399 by Assmus et al. Although in this patent no indications were made that this formulation belongs to a broader class of interpolymer complex adhesives, we consider the Example 9 of present invention as a reference. As has been noted by Assmus et al., adhesive properties of the blends are the function of their compositions. In order to obtain the tools manipulating the adhesion and to offer a range of others adhesives that were not yet disclosed in literature, in this example we have to gain an insight into the functions of every blend component in the control of adhesion.

Characteristics of tensile stress-strain curves make possible the evaluation of cohesive strength in terms of ultimate tensile stress under fracture of adhesive film, whereas free volume may be assessed qualitatively in terms of maximum elongation wider rupture. The area under stress-strain curve represents the work of viscoelastic polymer deformation up to break, and this value correlates to the work of adhesive debonding (see Feldstein M. M. "*Molecular Fundamentals of Pressure-Sensitive Adhesion*" in Benedek I. "*Development and Manufacture of Pressure-Sensitive Products*", Marcel Dekker, N.Y., 2005, Chapter 4, pp. 179-215. As follows from the tensile stress-strain curves in FIG. 5, mixing the film-forming polymer with ladder-like crosslinker in a ratio of [FFP]:[LLC]=10:1 leads to dramatic increase of cohesive strength (the value of ultimate stress increases by 6.6 times), whereas the free volume drops appreciably (the value of maximum elongation decreases by a factor of 4.3).

Adhesive properties of binary Eudragit E-100 and Eudragit L-100-55 blends with appropriate plasticizers were the subjects of U.S. Pat. No. 5,133,970 by Petereit & Roth and U.S. Pat. No. 5,296,512 by Beier et al., respectively. As the results of probe tack testing have shown (FIG. 6), at comparatively low plasticizer concentration (25 wt. %) the blend of Eudragit E-100 and Eudragit L-100-55 copolymers exhibits low tack and adhesive mechanism of debonding without fibrillation. With the rise of plasticizer content, the peak stress grows rapidly achieving the maximum at 35-45 wt. % of TEC. Respectively, and maximum elongation at probe detachment increases. However, if a peak value of stress passes through maximum at 35-45 wt. % of plasticizer concentration, the total amount of dissipated energy has maximum at 45-50 wt. % of TEC, when fibrillation process is much more elaborated and the blend demonstrates appreciable elongational flow. Following increase in the plasticizer concentration leads to cohesively weak compositions, which leave a remainder of adhesive on probe surface upon debonding.

Technology of polymer blends enables easy manipulating the specific balance between the cohesive strength and fluidity of adhesive composite by the increase in the content of ladder-like crosslinker. As follows from the stress-strain curves presented in FIG. 7, binary blend of the film-forming polymer (Eudragit E-100) with 35 wt. % of plasticizer TEC that contains no crosslinker is highly tacky fluid and debonds cohesively at high values of relative elongation leaving the remainder of the adhesive at the surface of probe. Mixing the film-forming polymer with complementary ladder-like crosslinker in a ratio of [FFP]:[LLC]=10:1 leads to immediate change of debonding mechanism from cohesive to adhesive, while the tack (maximum stress) is mainly controlled by the film-forming polymer.

EXAMPLE 2

Figure 8:
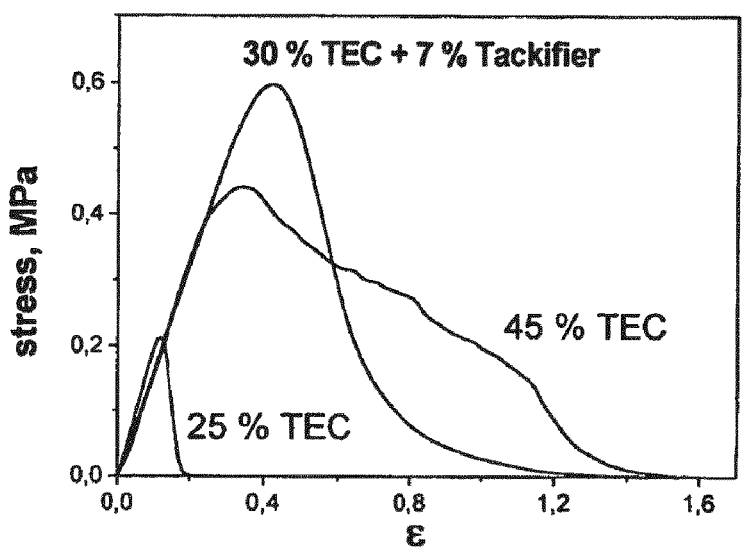
FIG. 8 compares the effects of plasticizer (TEC) and tackifier (glycerol ester of tall oil rosin) on probe tack stress-strain curves of amphiphilic adhesives based on the ladder-like electrostatic complex of Eudragit E-100 and Eudragit L-100-55 copolymers (10:1).

Improvement of Adhesion of the Ladder-Like Plasticized Interpolymer Complex by Incorporation of Tackifiers U.S. Pat. No. 6,063,399 by Assmus et al. does not describe all the tools necessary to enhance the adhesion of triple Eudragit E-100-Eudragit L-100-55-TEC blends. One of such tools is mixing the Eudragit E-100-Eudragit L-100-55-TEC blends with tackifiers. Owing to optimum hydrophilic-hydrophobic balance, the amphiphilic adhesives based on Eudragit E-100-Eudragit L-100-55 complexes turned out to be miscible with tackifiers, which are extensively used in adhesive technology to improve tack. As follows from the data shown in Table and FIG. 8, adding the tackifier Sylvagum RE 85K (glycerol ester of tall oil rosin) improves essentially the adhesive performance of blended adhesive. While plasticizers contribute mainly to the increase of material capability to develop large deformations under detaching stress, the tackifier enhances appreciably its cohesive strength by the increase in $\sigma_{max}$ value.

| Ex. No. | FFP | LLC | Plasticizer | Tackifier | $W_{deb}$, J/m² | $\sigma_{max}$, MPa |
|---|---|---|---|---|---|---|
| 2a | Eudragit E-100, 59.1 | None | Acetyl-tributyl Citrate, 35 | SYLVAGUM RE85K, Resin, 5.9 | 104 | 0.6 |
| 2b | Eudragit E-100, 57.3 | Eudragit L 100-55, 5.7 | Triethyl citrate, 30 | SYLVAGUM RE85K, Resin, 7 | 32 | 0.6 |
| 2c | Eudragit E-100, 61.8 | Eudragit L 100-55, 6.2 | Triethyl citrate, 25 | SYLVAGUM RE85K, Resin, 7 | 20 | 0.66 |
| 2d | Eudragit E-100, 70.9 | Eudragit L 100-55, 7.1 | Triethyl citrate, 15 | SYLVAGUM RE85K, Resin, 7 | | |

Figure 9:
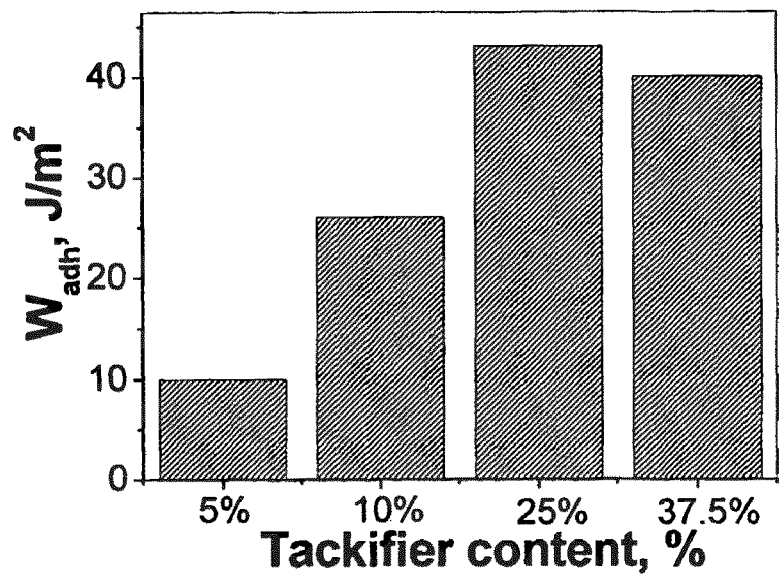
FIG. 9 shows the impact of tackifier content on the work of adhesive debonding for the blends of Eudragit E-100 with 25 wt. % of ATBC.

The data presented by Examples 2e-2g and illustrated in FIG. 9 demonstrate the effect of tackifier concentration (SYLVAGUM RE85K Resin) on adhesive properties of FFP, Eudragit E-100, plasticized with 25 wt % of ATBC in the absence of any LLC. Adding the tackifier results in the increase of tack that goes through a maximum at 25% SYLVAGUM concentration.

| Ex. No. | FFP | Plasticizer | Tackifier | $W_{deb}$, J/m² | $\sigma_{max}$, MPa |
|---|---|---|---|---|---|
| 2e | Eudragit E-100, 70 | Acetyltributyl Citrate, 25 | SYLVAGUM RE85K, Resin, 5 | 10 | 0.48 |
| 2f | Eudragit E-100, 60 | Acetyltributyl Citrate, 25 | SYLVAGUM RE85K, Resin, 15 | 26 | 0.8 |
| 2g | Eudragit E-100, 50 | Acetyltributyl Citrate, 25 | SYLVAGUM RE85K, Resin, 25 | 43 | 0.97 |

Examples 2h-2i exhibit how dramatic is the gain in adhesion if using the tackifier SYLVAGUM is accompanied with the increase of plasticizer concentration.

| Ex. No. | FFP | Plasticizer | Tackifier | $W_{deb}$, J/m² | $\sigma_{max}$, MPa |
|---|---|---|---|---|---|
| 2h | Eudragit E-100, 68.2 | Acetyltributyl Citrate, 25 | SYLVAGUM RE85K, Resin, 6.8 | 11 | 0.4 |
| 2i | Eudragit E-100, 59.1 | Acetyltributyl Citrate, 35 | SYLVAGUM RE85K, Resin, 5.9 | 104 | 0.6 |

Examples 2k-2m demonstrate how the adhesion of Eudragit E-100-Eudragit L-100 55 blends (10:1) may be optimized by the combined effect of the plasticizer and the tackifier:

| Ex. No. | FFP | LLC | Plasticizer | Tackifier | $W_{deb}$, J/m² | $\sigma_{max}$, MPa |
|---|---|---|---|---|---|---|
| 2k | Eudragit E-100, 57.3 | Eudragit L-100-55, 5.7 | Triethyl Citrate, 30 | SYLVAGUM RE85K, Resin, 7 | 32 | 0.6 |
| 2l | Eudragit E-100, 61.8 | Eudragit L-100-55, 6.2 | Triethyl Citrate, 25 | SYLVAGUM RE85K, Resin, 7 | 20 | 0.66 |
| 2m | Eudragit E-100, 52.4 | Eudragit L-100-55, 2.6 | Triethyl Citrate, 25 | SYLVAGUM RE85K, Resin, 5.9 | 120 | 1.23 |

Figure 10:
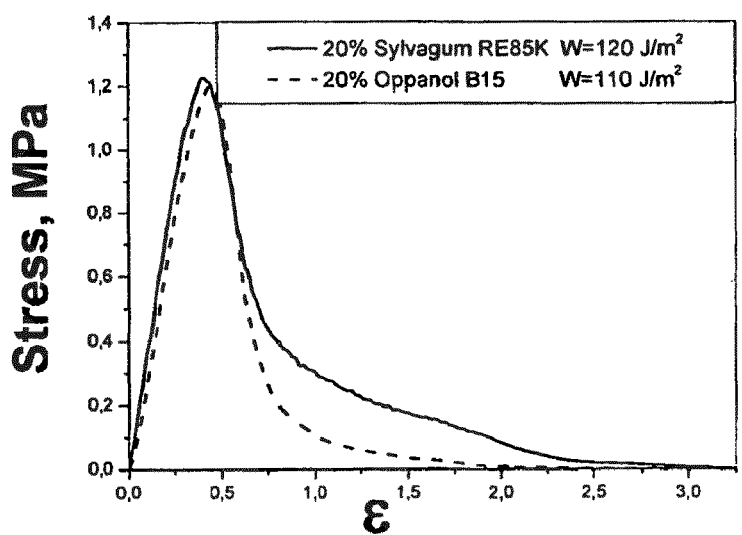
FIG. 10 compares the effects of two tackifiers—Sylvagum RE 85K rosin and PIB (Oppanol B-15) on probe tack of Eudragit E-100-Eudragit L-100-55 blends (10:1), plasticized with 25 wt. % of TEC.

As is seen from the data presented in FIG. 10, SYLVAGUM Resin is not a single tackifier that is miscible with Eudragit E-100-Eudragit L-100-55 ladder-like electrostatic complex, plasticized with TEC. An alternative tackifier, which is miscible with this blend, is Oppanol B15, a PIB of average molecular weight 75,000 g/mol.

EXAMPLE 3

Figure 11:
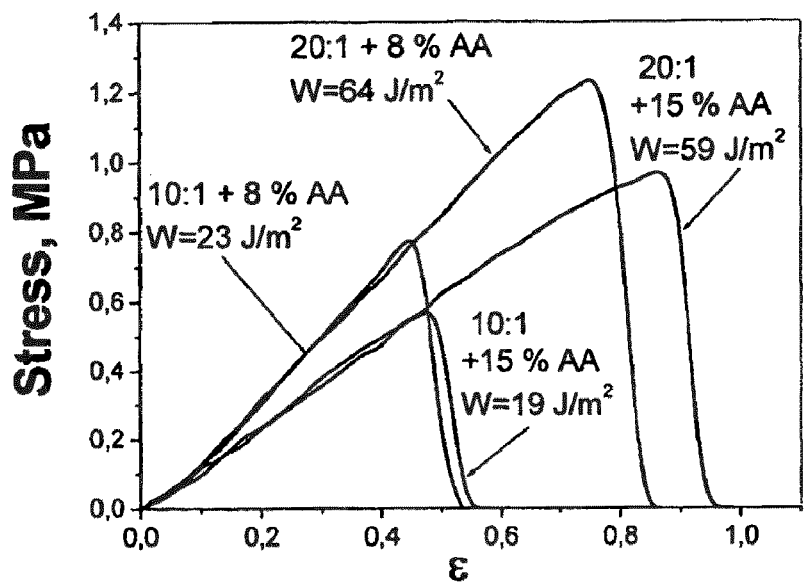
FIG. 11 demonstrates the effect of adipic acid on adhesive properties of Eudragit E-100/L100-55 blends with 25% of TEC at different E100/L100-55 ratios.

Adhesive Compositions Based on the Carcass-Like Complex of Eudragit E-100 Polybase and its Combination with the Ladder-Like Electrostatic Crosslinking The film forming polymer, exemplified in this description with Eudragit E-100 polybase, may be converted into the form of pressure sensitive adhesive not only by plasticizing with TEC, but and by adding into this blend higher carboxylic acids having 8 to 20 carbon atoms and dicarboxylic acids having 2 to 8 carbon atoms (U.S. Pat. No. 5,113,970 to Petereit and Roth). As follows from the data presented in Table Ex. 3 (see examples 3a and 3b), the blends of Eudragit E-100 with TEC and adipic acid (AA, dicarboxylic acid having 6 carbon atoms) are good skin contact adhesives. Forming two electrostatic bonds through both terminal carboxyl groups at AA short chain, the AA acts as the carcass-like crosslinker of trialkylamino groups in Eudragit E-100 polybase. Additional incorporation of AA into the plasticized ladder-like Eudragit E-100-Eudragit L-100-55 complex gives the blends outlined by Ex. 3c-3f (FIG. 11), which are good bioadhesives demonstrating the tack to highly moistened biological substrates such as teeth and oral mucosa. As is evident from the probe tack curves presented in FIG. 11, the less the content of the LLC (Eudragit L-100-55), the higher the adhesion. Because the junctions of carcass-like network consist of single electrostatic bonds in contrast to the ladder-like network, where the junctions are composed of a sequence of multiple bonds (see scheme in FIG. 4), the carcass like network can be easier ruptured and reformed than the ladder-like network. For this reason the adhesives involving, the carcass-like type of non-covalent crosslinking are much easier soluble in water than the structures based on the ladder-like complex.

TABLE EXAMPLE 3

Properties of compositions involving adipic acid (AA) as a carcass-like crosslinker of Eudragit E-100 polybase.

| Example No | Components | Ratios, % wt | SF, % buffer pH = 5.6 | SR | Adhesion to teeth | cheek | gums | arm | $W_{adh}$, J/m² | $\sigma_{max}$, MPa |
|---|---|---|---|---|---|---|---|---|---|---|
| 3a | Eu E-100 | 67 | FD* | | YES | NO | NO | YES | 200 | 1.25 |
| | Adipic acid | 8 | | | | | | | | |
| | TEC | 25 | | | | | | | | |
| 3b | Eu E-100 | 60 | FD | | YES | NO | YES | YES | 150 | 0.9 |
| | Adipic acid | 15 | | | | | | | | |
| | TEC | 25 | | | | | | | | |
| 3c | Eu E-100 | 61 | 73.6 | 3.6 | YES | YES | YES | NO | 23 | 0.8 |
| | Eu L-100-55 | 6 | | | | | | | | |
| | Adipic acid | 8 | | | | | | | | |
| | TEC | 25 | | | | | | | | |
| 3d | Eu E-100 | 54.5 | FD | | YES | YES | YES | NO | 19 | 0.6 |
| | Eu L-100-55 | 5.5 | | | | | | | | |
| | Adipic acid | 15 | | | | | | | | |
| | TEC | 25 | | | | | | | | |
| 3e | Eu E-100 | 63.8 | FD | | YES | NO | NO | NO | 64 | 1.26 |
| | Eu L-100-55 | 3.2 | | | | | | | | |
| | Adipic acid | 8 | | | | | | | | |
| | TEC | 25 | | | | | | | | |
| 3f | Eu E-100 | 57 | FD | | YES | NO | NO | NO | 59 | 0.99 |
| | Eu L-100-55 | 3 | | | | | | | | |
| | Adipic acid | 15 | | | | | | | | |
| | TEC | 25 | | | | | | | | |

*Fully dissolving

Other appropriate carcass-like crosslinkers of Eudragit E-100 FFP have been found to be PEG-dicarboxylic acid and diacids having 2 to 6 carbon atoms between the carboxyl groups.

EXAMPLE 4

Enhancement of Adhesion by Partial Ionization of Film-Forming Eudragit E-100 Polymer and Ladder-Like Crosslinker (Eudragit L-100-55)

Another and highly effective tool to enhance the adhesion of Eudragit E-100-Eudragit L-100-55-TEC blends, which also is not explored by the above mentioned U.S. Pat. No. 6,063,399 by Assmus et al., is outlined by salutary impact of partial ionization of polyelectrolyte macromolecules within the interpolymer complex. The amphiphilic adhesives based on Eudragit E-100-Eudragit L-100-55 blends involve two complementary polyelectrolytes: polyacid and polybase. The film-forming polymer, Eudragit E-100, represents the latter. Accordingly, the adhesion of Eudragit E-100-Eudragit L-100-55 adhesives can be affected by partial ionization of both polyacid and polybase macromolecules.

Figure 12:
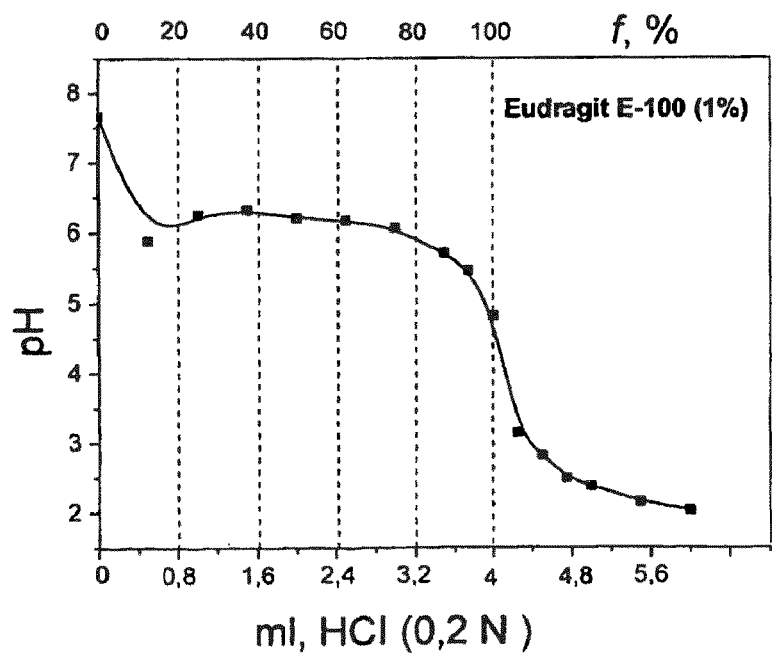
FIG. 12 represents the curve of potentiometric titration of 1% aqueous solution of Eudragit E-100 polybase with 0.2 N HCl. The ionization degree, f, is plotted along a top axis.
Figure 13:
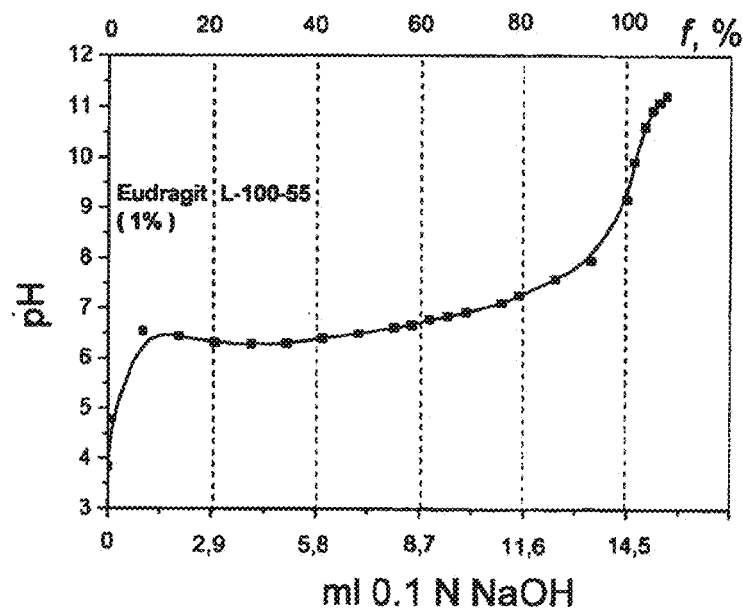
FIG. 13 represents the curve of potentiometric titration of 1% aqueous solution of Eudragit L-100-55 polyacid with 0.1 N NaOH. The ionization degree, f, is plotted along a top axis.

FIGS. 12 and 13 illustrate the procedure of partial ionization of the Eudragit E-100 polybase and Eudragit L-100-55 polybase with corresponding amounts of neutralizing agents, HCl and NaOH respectively. In order to determine the amounts of acid and alkali needed for partial ionization of relevant polyelectrolyte to desirable extent, titration curve first must be measured. Taking into account that the jump in pH corresponds to 100% ionization of the polyelectrolyte, the amount of neutralizing agent needed for 20% ionization of the polyelectrolyte constitutes a fifth fraction of total (equivalent) amount of the acid or alkali.

As is evident from the data presented in Table Ex. 4, the tack is essentially improved with treatment of Eudragit L100-55 by NaOH solution. The tack improvement becomes comparatively negligible as ionization degree exceeds 5%.

TABLE EXAMPLE 4

| Ex. No. | FFP | LLC | Plasticizer | pH modifier | $W_{deb}$, J/m² | $\sigma_{max}$, MPa |
|---|---|---|---|---|---|---|
| 4a | Eudragit E-100, 61.8 | Eudragit L 100-55, 6.2 | Triethyl citrate, 25 | NaOH 5% ionization | 18.5 | 0.73 |
| 4b | Eudragit E-100, 61.8 | Eudragit L 100-55, 6.2 | Triethyl citrate, 25 | NaOH 10% ionization | 20 | 0.77 |
| 4c | Eudragit E-100, 59.1 | Eudragit L 100-55, 5.9 | Triethyl citrate, 35 | NaOH 5% ionization | 54 | 0.83 |
| 4d | Eudragit E-100, 59.1 | Eudragit L 100-55, 5.9 | Triethyl citrate, 35 | NaOH 10% ionization | 57 | 0.97 |
| 4e | Eudragit E-100, 61.8 | Eudragit L 100-55, 6.2 | Triethyl citrate, 25 | HCl 5% ionization | 23 | 0.82 |
| 4f | Eudragit E-100, 61.8 | Eudragit L 100-55, 6.2 | Triethyl citrate, 25 | HCl 10% ionization | 68 | 1.3 |
| 4g | Eudragit E-100, 59.1 | Eudragit L 100-55, 5.9 | Triethyl citrate, 35 | HCl 5% ionization | 50 | 0.82 |
| 4h | Eudragit E-100, 59.1 | Eudragit L 100-55, 5.9 | Triethyl citrate, 35 | HCl 10% ionization | 77 | 0.93 |

Figure 14:
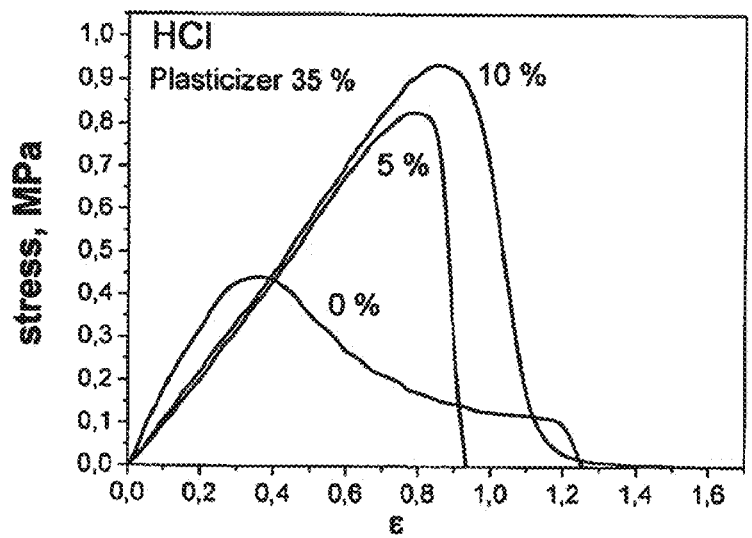
FIG. 14 demonstrates the effect of partial ionization of film-forming polymer (Eudragit E-100) by HCl solution on the tack of amphiphilic adhesive containing 35 wt. % of plasticizer TEC.

As is seen from the stress-strain curves in FIG. 14, for comparatively ductile adhesives (exemplified here by the composition containing 35 wt. % of plasticizer), which reveal fibrillation (a plateau on the stress-strain curves), partial ionization of film-forming polybase Eudragit E-100 by HCl solution enhances the cohesive strength dramatically and the adhesive debonds without fibrillation. The maximum elongation in the point of debonding first decreases with 5% ionization and then increases again (at 10% ionization), implying that under comparatively small degree of polymer chain ionization the enhancement of cohesive strength is a predominant factor, whereas further increase in the ionization degree is accompanied with formation of large free volume. The enhancement of cohesive strength tends to a maximum above 10% of the ionization of film-forming polymer.

Figure 15:
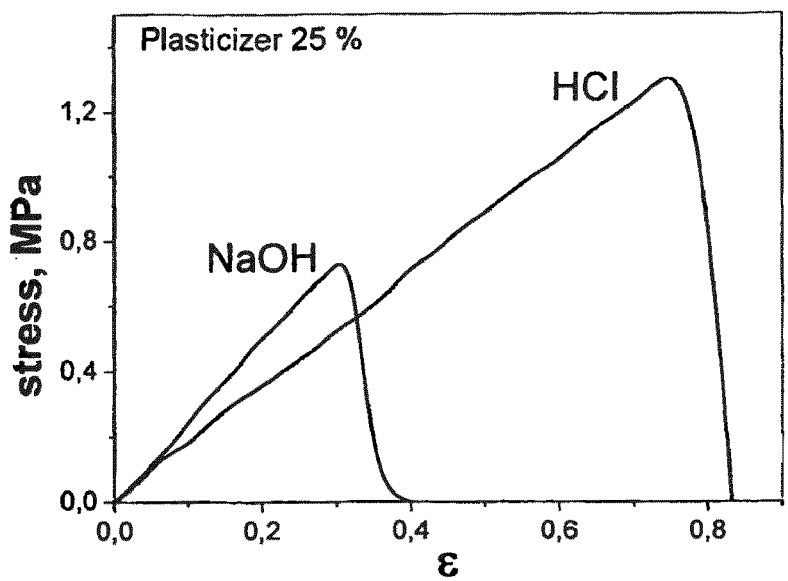
FIG. 15 compares the effects of partial ionization of film-forming polymer (by NCI) and ladder-like crosslinker (by NaOH) on the probe tack stress-strain curves for amphiphilic Eudragit E-100-Eudragit L-100-55 adhesive containing 25 wt., % of plasticizer TEC.

By comparing the probe tack data presented in FIG. 14, 15 and in the Table Ex. 4, it may be seen that qualitatively the mechanisms of tack enhancement by ionization of the ladder-like crosslinker and the film-forming polymer are similar. However, as follows from the data shown in FIG. 15, in quantitative terms the effect of ionization of the film-forming polybase on adhesion is much stronger than that observed for the ladder-like crosslinking polyacid.

Figure 16:
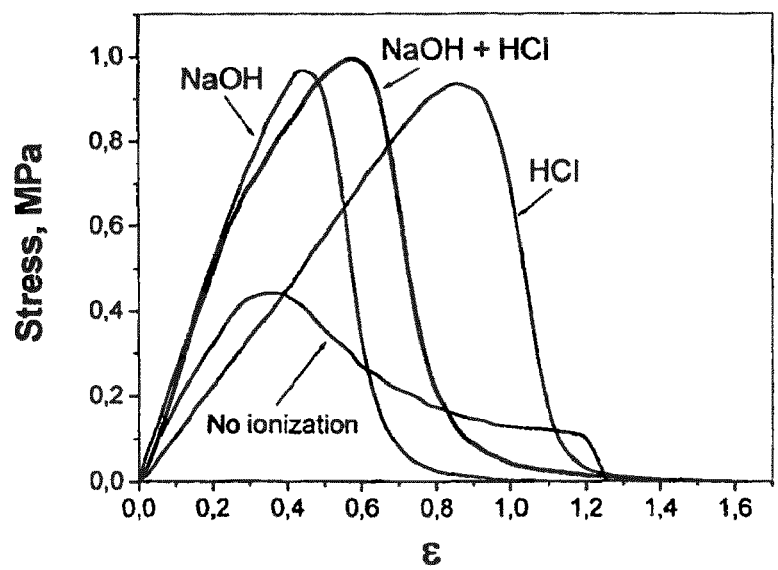
FIG. 16 represents probe tack stress-strain curves for the Eudragit E-100-Eudragit L-100-55 complex containing 35 wt. % of plasticizer TEC under 10% ionization of film-forming polymer and ladder-like crosslinker and for the complex formed between partly ionized polymer components at 10% degree of ionization.

If both the film-forming polymer and the ladder-like crosslinker are preliminary ionized by treating respectively with HCl and NaOH solutions, then the ionic bonding between cationic groups of Eudragit E-100 copolymer and anionic groups of Eudragit L-10055 copolymer contributes to the adhesive behavior of the interpolymer complex along with hydrogen bonds formed between uncharged groups. As follows from the data shown in FIG. 16, in this case the adhesive properties of the complex are intermediate between those featured for the complex involving partial ionization of either the film-forming polymer or the ladder-like crosslinker.

Effects of macromolecular ionization on the tack of adhesive composites involving polyelectrolytes have never been earlier reported.

Partial 10% ionization of the ladder-like crosslinker (Eudragit L-100-55) in interpolymer complex with film-forming Eudragit E-100 polymer does not affect the swelling and dissolution of the adhesive. However, the 10% ionization of the film-forming polymer with HCl solution results in appreciable increase of swell ratio from 3.5 to 22.5, while the amount of soluble fraction has comparatively insignificant effect on the value of sol fraction.

If the polybase and polyacid in the ladder-like Eudragit E-100-Eudragit L-100-55 complex are interchanged in such a way that the polyacid (Eudragit L-100-55) serves as the film-forming polymer and the polybase (Eudragit E-100) is the ladder-like crosslinker, adhesive materials wherein the treatment with NaOH has a greater effect on adhesion and sorption are obtained.

EXAMPLE 5

Figure 3:
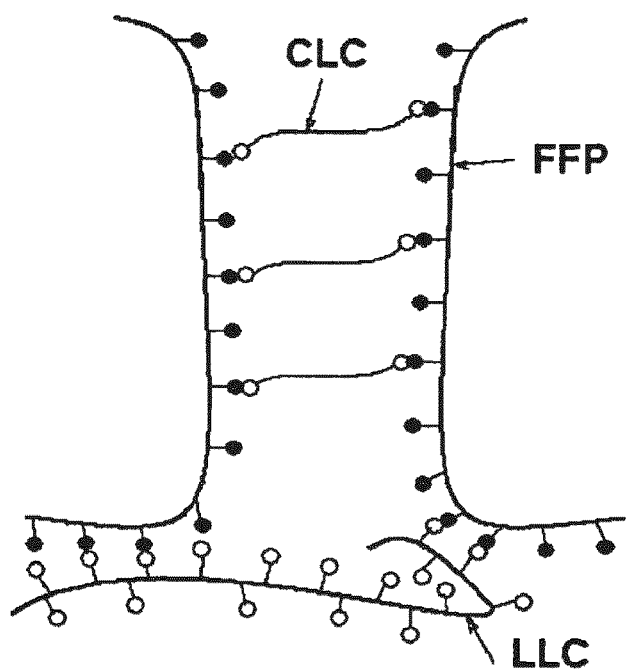
FIG. 3 schematically illustrates an interpolymer complex combining carcass-like and ladder-like types of crosslinking. "FFP" represents a film-forming polymer, "CCL" represents a carcass-like crosslinker, and "LLC" represents a ladder-like crosslinker.

Improvement of Adhesion of PVP-PEG-Eudragit L-100-55 Blends by Means of Partial Ionization of the Ladder-Like Crosslinker The hydrogen bonded interpolymer complexes combining the ladder-like and carcass-like types of noncovalent crosslinking, shown in schematic form in FIG. 3, share the properties of pressure-sensitive adhesives and bioadhesives (see U.S. patent application Ser. No. 10/936,887 to Feldstein et al. for "Method of Preparing Polymeric Adhesive Compositions Utilizing the Mechanism of Interaction Between The Polymer Components, filed Sep. 8, 2004). The effect of partial ionization of Eudragit L100-55 on adhesive properties of PVP/PEG/Eudragit L100-55 is demonstrated by present example.

Preparation of films. 30 g of PEG400 was dissolved in 280 g of water/ethanol (1:1) mixture. Required amount of sodium hydroxide was dissolved (as indicated in the Table Ex-5.). Under vigorous stirring 12 g of Eudragit L100-55 powder was added followed by adding 58 g of PVP (K90) powder. The mixture was stirred over 2 hours to obtain homogeneous solution. The solution was stored over 5 hours to let air bubbles dissipate. Polymer films were prepared by solution casting onto a PET backing with following drying at ambient temperature over 3 days. Films of 0.20±0.04 mm in thickness were obtained. Water content in the films was measured gravimetrically by weight loss at 120° C. Films with hydration degree 12±0.5 wt % were obtained.

TABLE EXAMPLE 5

|  | PVP, grams | PEG 400, grams | Eudragit L100-55, grams | NaOH, grams | Eudragit L100-55 |
|---|---|---|---|---|---|
| Ex 5-1 | 58 | 30 | 12 | 0 | 0 |
| Ex 5-2 | 58 | 30 | 12 | 0.129 | 5 |
| Ex 5-3 | 58 | 30 | 12 | 0.258 | 10 |
| Ex 5-4 | 58 | 30 | 12 | 0.516 | 20 |

Figure 17:
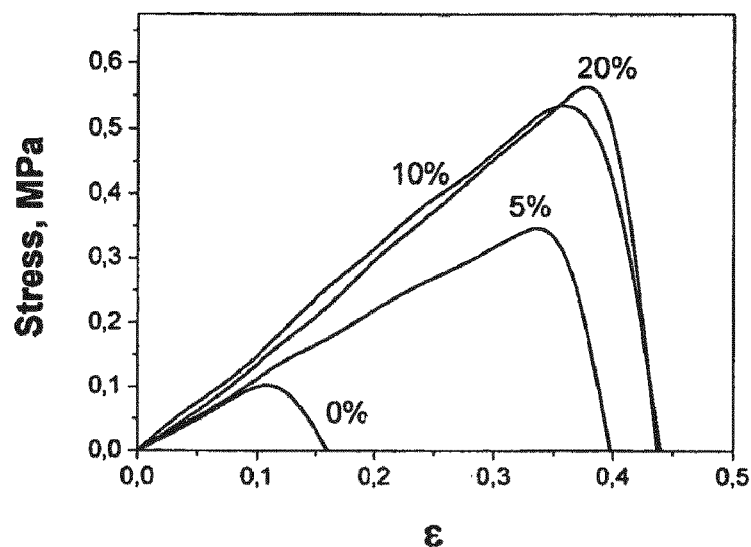
FIG. 17 represents the effect of partial ionization of carboxyl groups in the ladder-like crosslinker on the stress-strain curves of the PVP-PEG-Eudragit L-100-55 adhesive hydrogel containing 12 wt. % of sorbed water. The degrees of ionization (%) are shown in the Figure.

As is obvious from the stress-strain curves in FIG. 17, partial ionization of the ladder-like crosslinker in the blends with PVP-PEG carcass-like complex improves the adhesion appreciably but does not change the mechanism of adhesive deformation under debonding process. The latter remains to be adhesive (no remainder of adhesive material at a probe surface upon debonding). Improvement of tack and adhesion tends to a maximum at 10% ionization of the ladder-like crosslinker. Such mechanism of tack improvement has been also established for the first time.

EXAMPLE 6

Others Adhesive Compositions Based on Plasticized Ladder-Like Interpolymer Complexes Eudragit E-100 is a typical and comparatively well-studied but not unique representative of polybases suitable for the formulation of adhesives based on the ladder-like interpolymer complexes with polyacids. Others appropriate polybases include homopolymers and copolymers of vinyl amine or chitosan among polyelectrolytes, and PVP or PNIPAM among non-polyelectrolytes. As an example, following Table outlines the adhesive properties of the blends of high molecular weight PVP K-90 (film-forming polymer) with Eudragit L-10055 as ladder-like crosslinker, plasticized with TEC. The inverted composition wherein the Eudragit L-100-55 serves as the film-forming polymer and the PVP as the ladder-like crosslinker was also prepared and characterized. These compositions differ from that described in Examples 1-3 by the lack of carcass-like crosslinker and, consequently, represent others examples of the adhesives based on ladder-like interpolymer complexes shown schematically in FIG. 4. The compositions were prepared by casting-drying method from ethanol solutions.

| Ex. No. | FFP | LLC | Plasticizer | $W_{deb}$, J/m² | $\sigma_{max}$, MPa |
|---|---|---|---|---|---|
| 6a | PVP K-90 60.2 | Eudragit L 100-55, 9.8 | Triethyl citrate, 30 | 24 | 0.77 |
| 6b | PVP K-90 50.1 | Eudragit L 100-55, 9.9 | Triethyl citrate, 40 | 55 | 0.97 |
| 6c | Eudragit L 100-55, 61.1 | PVP K-90 10.9 | Triethyl citrate, 30 | 44 | 0.80 |

Figure 18:
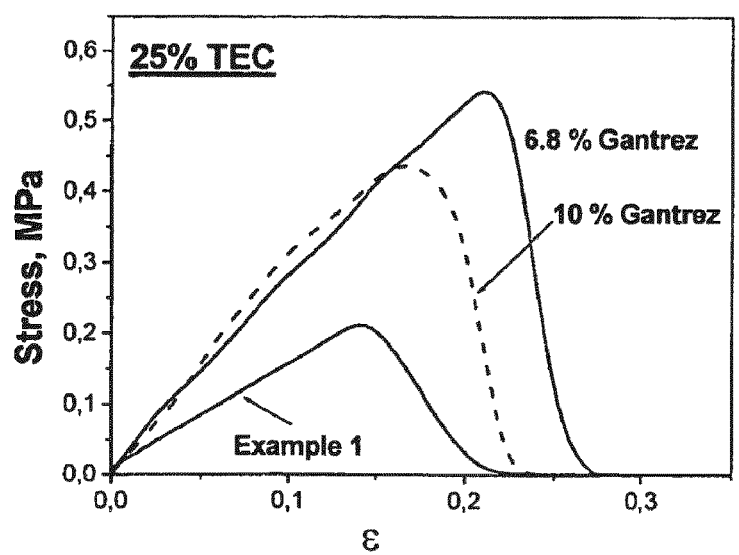
FIG. 18 compares the adhesive properties of interpolymer complexes of Eudragit E-100 film-forming polymer with the ladder-like crosslinkers of different hydrophilicity: Eudragit L-100-55 (Example 9) and Gantrez S-97. The content of plasticizer TEC in blends is 25 wt. %.

In following composition the Eudragit E-100 was selected as film-forming polymer (polybase) and Gantrez S-97 as the ladder-like crosslinker (polyacid). The latter is a copolymer of maleic acid with methylvinyl ether (1:1). TEC was used as plasticizer. Under vigorous stirring the powder of Gantrez S-97 polymer was slowly added into the 30% ethyl alcohol solution of Eudragit E-100, that was previously mixed with TEC (plasticizer), until a homogeneous dispersion was obtained. The semitransparent, homogeneous film was obtained using simple casting and drying procedure of the previously obtained dispersion under ambient temperature. Prepared films contained 25 wt % of TEC, while Eudragit E-100-Gantrez S-97 ratio was varied. FIG. 18 compares the probe tack stress-strain curves for the Eudragit E-100-Gantrez S-97 ladder-like complex with the curve featured for Eudragit E-100-Eudragit L-100-55 composition plasticized with equivalent amount of TEC.

As follows from the curves demonstrated in FIG. 18, replacement of the Eudragit L-100-55 ladder-like crosslinker in the complex with Eudragit E-100 film-forming polymer for much more hydrophilic Gantrez S-97 copolymer improves the tack significantly.

Figure 19:
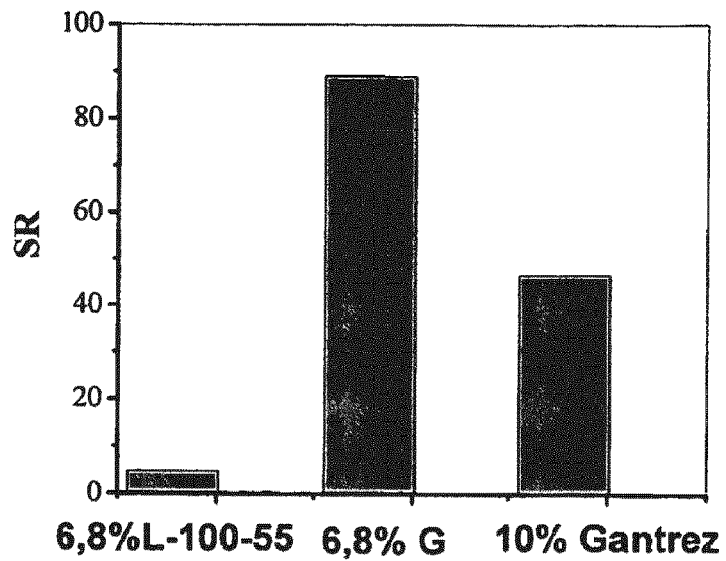
FIG. 19 demonstrates the effect of ladder-like crosslinker (Eudragit L-100-55 or Gantrez S-97) on water absorbing capacity, expressed in terms of Swell Ratio, for Eudragit E-100 blends, plasticized with 25% of TEC.

While the water-absorbing capacity (measured in terms of Swell Ratio, SR, which is a ratio of the weight of gel in swollen state to the dry weight of gel fraction) for amphiphilic adhesives based on plasticized ladder-like Eudragit E-100-Eudragit L-100-55 complexes is comparatively low, ranging from 3 to 6 in dependence on composition, it dramatically affected by the nature of the ladder-like crosslinker. As the data in FIG. 19 have shown, replacement of comparatively hydrophobic Eudragit L-100-55 by much more hydrophilic Gantrez S-97 leads to the increase of Swell Ratio from 4.4 to 89.2. In this way, moderately absorbing adhesive compositions based on the ladder-like complexes may be easily modified to give super-absorbing adhesives. The super-absorbing adhesives, outlined by this invention, represent a new class of pharmaceutical materials.

Other suitable ladder-like crosslinkers for Eudragit L-100-55 polymer are alginic acids and carboxyl-containing cellulose derivatives such as HPMCP. Their mixing with Eudragit L-100-55 in solutions can be significantly facilitated by partial ionization of relevant polymers.

Eudragit E-100 is not unique polybase that can be used as FFP in the blends with Eudragit L-100-55 polybase. Other suitable candidates as FFP in plasticized ladder-like complexes are the Eudragit RS and Eudragit RL. The Eudragit RS is a copolymer of trimethylammonioethylmethacrylate chloride (0.1) with ethylacrylate (1) and methylmethacrylate (2), available from Rain Pharma Polymers. The Eudragit RL is a copolymer of trimethylammonioethyl methacrylate chloride with ethylacrylate and methylmethacrylate (0.2:1:2), available from Rohm Pharma Polymers as well. Although both TL and RS polymer contain ionic groups, they are insoluble in water due to high concentration of hydrophobic polymer units. The Eudragit RL and RS polymers are capable to form ionic bonds with polymer units bearing negative charge (carboxylate anions), Appropriate ladder-like crosslinker for such polymers is ionized Eudragit L-100-55, Next Table demonstrates the composition of adhesive blend prepared using Eudragit RL and Eudragit RS polymers:

| Composition | % wt. |
| --- | --- |
| Eudragit RL | 49.1 |
| Eudragit RS | 16.4 |
| TEC | 28.0 |
| Eudragit L100-55 | 6.5 |
| Fully ionized | |

Under vigorous stirring the appropriate amount of Eudragit RL was dissolved in the ethanol solution of Eudragit RS. Under stirring the required amount of the plasticizer tributyl citrate (TBC) was added into the ethanol solution of two base polymers Eudragit RL and Eudragit RS. Fully ionized Eudragit L100-55 was then dissolved in the blend of Eudragit RL/Eudragit RS/TBC. The homogeneous film was obtained using casting and drying procedure of the previously obtained solution. Prepared composition feature the values of Sol fraction of 4.3% and Swell ratio of 2.5. The homogeneous film is initially nontacky but adheres strongly to teeth surface providing good adhesive contact that is stable during 4 hours.
[000155] Another appropriate polybase forming the ladder-like complexes with polyacids is chitosan.

EXAMPLE 7

Figure 20:
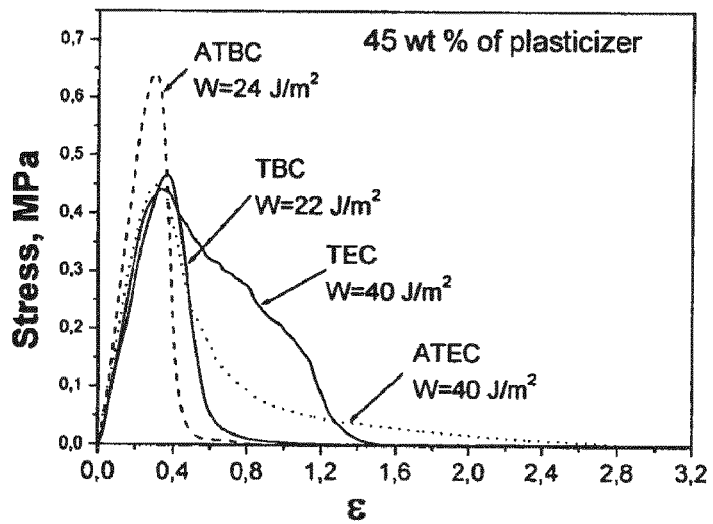
FIG. 20 exhibits the impact of the nature of plasticizers (TEC, ATEC, TBC and ATBC) on probe tack properties of Eudragit E-100-Eudragit L-100-55 complexes. Concentration of the plasticizers is 45 wt %.
Figure 21:
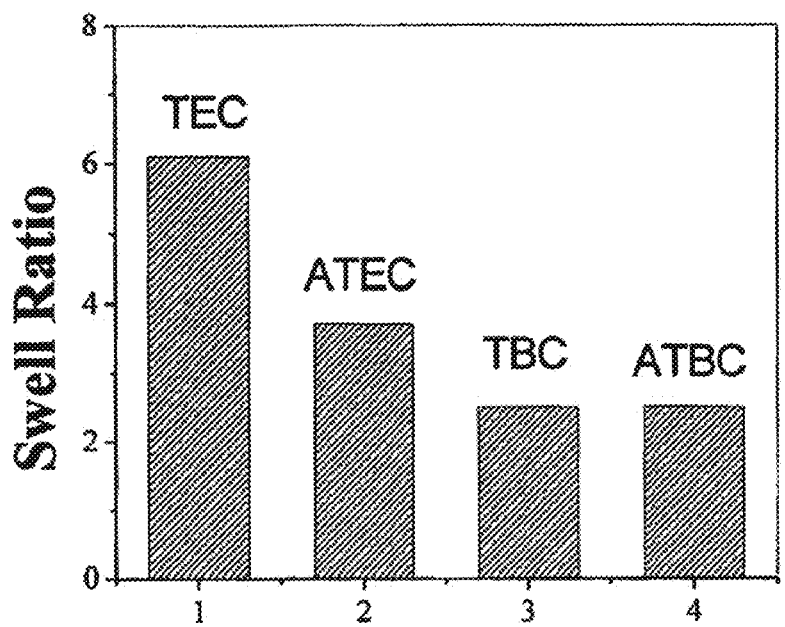
FIG. 21 illustrates the influence of the nature of plasticizer in Eudragit E-100-Eudragit L-100-55 complex on Swell Ratio of relevant blends.

Effect of the Nature of Plasticizers on Adhesive Properties and Water-Absorbing Capacity of Eudragit E-100-Eudragit L-100-55 Complex FIGS. 20 and 21 illustrate the influence of hydrophilicity of plasticizers on the adhesive and water absorption properties of the compositions based on the interpolymer complex between Eudragit E-100 polybase Eudragit L-100-55 polyacid. As is evident from the probe tack profiles presented in FIG. 20, more hydrophilic plasticizers (TEC and ATEC) demonstrate more ductile mechanism of deformation under debonding stress, developing higher values of maximum elongation compared to more hydrophobic TBC and TBC, which behave like solid adhesives and deform without fibrillation. The adhesion, measured in terms of the work of debonding, decreases in a row ATEC z, TEC>ATBC>TBC.

Correspondingly, the swell ratio of the blends of Eudragit E100-Eudragit L100-55 with plasticizers TEC, ATEC, TBC, ATBC, decreases with the decrease in their hydrophilicity in the row TEC>ATEC>TBC>ATBC. It is worthy of note, that the nature of plasticizers affects the water absorbing capacity in a smaller extent than the adhesion.

EXAMPLE 8

Hydrophilization of Amphiphilic Adhesives Based on Eudragit E-100-Eudragit L-100-55 Complexes As has been shown above, adhesive blends based on plasticized Eudragit E-100-Eudragit L-100-55 complexes are miscible with such hydrophobic plasticizers and tackifiers as PIB (Oppanol B-15) (See FIG. 10). Because the monomer units in Eudragit E-100-Eudragit L-100-55 complexes combine polar hydrophilic and non-polar lipophilic entities, these adhesives belong to the class of amphiphilic materials and are also miscible with hydrophilic and even hygroscopic polymers and filers. Hydrophilization of amphiphilic Eudragit E-100-Eudragit L-100-55 adhesives represents an important tool to enhance their water-absorbing capacity and modify the adhesion.

Figure 22:
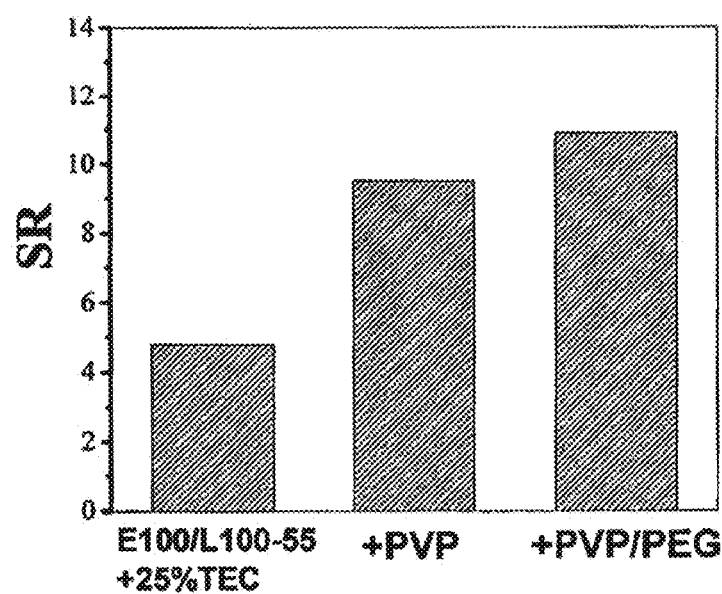
FIG. 22 shows the effect of mixing the Eudragit E-100-Eudragit L-100-55 complexes with PVP and with PVP-PEG blend (2:1) on water absorbing capacity expressed in terms of Swell Ratio.
Figure 23:
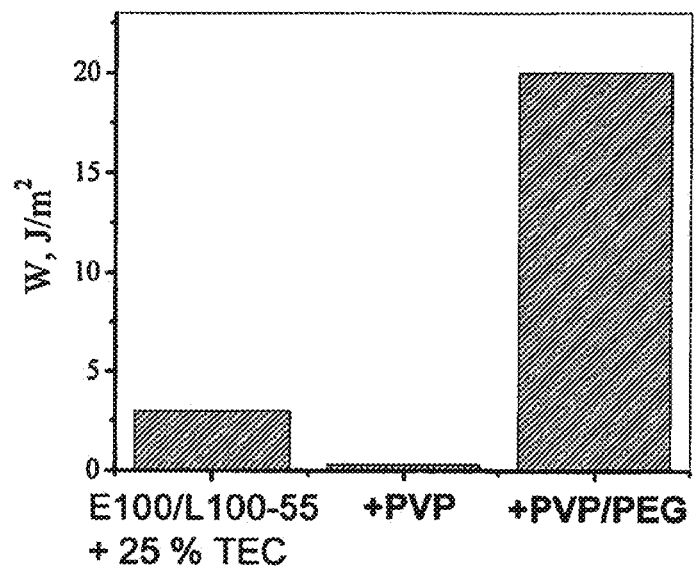
FIG. 23 demonstrates the influence of hydrophilization of Eudragit E-100-Eudragit L-100-55 plasticized complex on the work of adhesive debonding (probe tack).

The data presented in Table Ex. 8.1 and shown in FIGS. 22 and 23 demonstrate the effect of mixing with hydrophilic PVP and with its adhesive blends with PEG-400 on adhesion and water absorbing capacity of Eudragit E-100-Eudragit L-100-55 interpolymer complex, plasticized with 25 wt. % of TEC. Under vigorous stirring, necessary amount of Eudragit L100-55 was dissolved in the ethanol solution of Eudragit E100. Then the plasticizer (TEC) was dissolved in the ethanol solution of two parent polymers. Under stirring the appropriate amount of low molecular weight PVP or low molecular weight PVP blend with PEG-400 was dissolved in the ethanol solution of E100/L100-55 blend with TEC. The films were obtained by casting drying procedure as described above.

TABLE EXAMPLE 8.1

Compositions and properties of Eudrafit E-100-Eudragit L-100-55 blends with plasticizer TEC and hydrophylizing agents, PVP and PVP-PEG

| Ex. No. | FFP | LLC | Plasticizer | Additive | Sol | SR | $W_{deb}$, J/m² | $\sigma_{max}$, MPa |
|---|---|---|---|---|---|---|---|---|
| 8a | Eudragit E-100, 58.0 | Eudragit L 100-55, 5.8 | Triethyl citrate 21.2 | PVP K 30, 15 | 53.4 | 9.5 | none | none |
| 8b | Eudragit E-100, 54.1 | Eudragit L 100-55, 5.4 | Triethyl citrate, 25.5 | PVP K 30, 15 | 51.7 | 8.1 | none | none |
| 8c | Eudragit E-100, 52.2 | Eudragit L 100-55, 5.2 | Triethyl citrate, 19.2 | PVP K 30 15  PEG 400 8.4 | 63.8 | 10.9 | 20 | 0.73 |
| 8d | Eudragit E-100, 48.7 | Eudragit L 100-55, 4.9 | Triethyl citrate, 23.0 | PVP K 30 15  PEG 400 8.4 | 60.5 | 7.1 | 59.7 | 0.98 |

The films of Eudragit E100/Eudragit L100-55/TEC blends with PVP K-30 were semitransparent indicating of their heterogeneous structure. These films had poor or no initial tack in contrast to the blends with PVP-PEG carcass-like complex (FIG. 23). These latter films were homogeneous and transparent.

As is evident from the data presented in Table Ex. 8.1 and FIG. 22, mixing with both PVP and PVP-PEG blends leads to an appreciable increase in water absorbing capacity of the adhesive materials, The data in Tables 8.2-8.5 illustrate other approaches towards adhesive materials of controlled water-absorbing capacity based on ladder-like interpolymer complexes.
Eudragit E100/TEC/Carbopol:

Preparation of films. Required amount of Eudragit E 100 was dissolved in ethyl acetate (3 parts of Eudragit E100 were dissolved in 7 parts of ethyl acetate). Required amount of TEC (as indicated in the Table 8.2) was added under vigorous stirring to obtain homogeneous solution (Solution I). In a separate jar required amount of Carbopol 974 (as indicated in the Table 8.2) was suspended in ethyl acetate (2 parts of Carbopol 974 were suspended in 5 parts of ethyl acetate) to obtain Solution II. Carbopol 974 is a chemically crosslinked polyacrylic acid. Different grades of Carbopol polymers are supplied with Noveon, Inc. In the form of finely micronized powder. Under vigorous stirring Solution II was added into Solution I, and the mixture was stirred over 20 min. Polymer films were prepared by solution casting onto a PET backing with following drying at ambient temperature over 3 days. Films of 0.15±0.04 mm in thickness were obtained,

TABLE EXAMPLE 8.2

| Example | Eudragit E100 | TEC | Carbopol 974 | Swell ratio |
|---|---|---|---|---|
| 1 | 65 | 25 | 10 | 4.6 |
| 2 | 55 | 25 | 20 | 12.8 |
| 3 | 45 | 25 | 30 | 20.4 |
| 4 | 40 | 30 | 30 | 23.7 |

In the examples 8.2 and 8.3 the Carbopol serves both as a ladder-like crosslinker and hydrophilizing agent.
Eudragit RS/RL/TEC/Carbopol Preparation of films. Required amounts of Eudragit RS, Eudragit RL (as indicated in the Table 8.3) were dissolved in ethyl acetate (3 parts of the sum of Eudragit RS and Eudragit RL were dissolved in 7 parts of ethyl acetate). Required amount of TEC (as indicated in the Table 8.3) was added under vigorous stirring to obtain homogeneous solution (Solution I). In a separate jar required amount of Carbopol 974 (as indicated in the Table 8.3) was suspended in ethyl acetate (2 parts of Carbopol 974 were suspended in 5 parts of ethyl acetate) to obtain Solution II. Under vigorous stirring Solution II was added into Solution I, and the mixture was stirred over 20 min. Polymer films were prepared by solution casting onto a PET backing with following drying at ambient temperature over 3 days. Films of 0.20±0.04 mm thickness were obtained.

TABLE EXAMPLE 8.3

| Ex. | Eudragit RS | Eudragit RL | TEC | Carbopol 974 | Swell ratio |
|---|---|---|---|---|---|
| 1 | 45 | 15 | 30 | 10 | 2.9 |
| 2 | 37.5 | 12.5 | 30 | 20 | 5.3 |
| 3 | 37.5 | 12.5 | 20 | 30 | 6.8 |
| 4 | 30 | 10 | 20 | 40 | 13.4 |

In the example 8.4 the Kollidon CLM serves as a ladder-like crosslinker and hydrophilizing agent.
Eudragit RS/RL/TEC/KowboN CLM Preparation of films. Required amounts of Eudragit RS, Eudragit RL (as indicated in the Table 8.4) were dissolved in ethyl acetate (3 parts of the sum of Eudragit RS and Eudragit RE were dissolved in 7 parts of ethyl acetate). Required amount of TEC (as indicated in the Table 8.4) was added under vigorous stirring to obtain homogeneous solution (Solution f). In a separate jar required amount of Kollidon CLM (as indicated in the Table 8.4) was suspended in ethyl acetate (2 parts of Kollidon CLM were suspended in 5 parts of ethyl acetate) to obtain Solution II. Kollidon CLM is physically crosslinked polyvinylpyrrolidone supplied with BASF in the form of finely micronized powder. Under vigorous stirring Solution II was added into Solution I, and the mixture was stirred over 20 min. Polymer films were prepared by solution casting onto a PET backing with following drying at ambient temperature over 3 days. Films of 0.20±0.04 mm thickness were obtained.

TABLE EXAMPLE 8.4

| Example | Eudragit RS | Eudragit RL | TEC | Kollidon CLM | Swell ratio |
|---|---|---|---|---|---|
| 1 | 45 | 15 | 30 | 10 | 2.3 |
| 2 | 41.25 | 13.75 | 30 | 15 | 3.1 |
| 3 | 45 | 15 | 20 | 20 | 4.0 |
| 4 | 37.5 | 12.5 | 20 | 30 | 4.8 |

In the example 8.5 the Cab-O-Sil M5 serves as a hydrophilizing agent.

Eudragit RS/RL/TEC/Cab-O-Sil M5

Preparation of films. Required amounts of Eudragit RS, Eudragit RL (as indicated in the Table 8.5) were dissolved in ethyl acetate (3 parts of the sum of Eudragit RS and Eudragit RL were dissolved in 7 parts of ethyl acetate), Required amount of TEC (as indicated in the Table 8.5) was added under vigorous stirring to obtain homogeneous solution (Solution I). In a separate jar required amount of Cab-O-Sil M5 (as indicated in the Table 8.5) was suspended in ethyl acetate (2 parts of Cab-O-Sil M5 were suspended in 5 parts of ethyl acetate) to obtain Solution II. Cab-O-Sil M5 is synthetic silicone dioxide supplied with Cabot Corporation in the form of finely micronized powder. Under vigorous stirring Solution II was added into Solution I, and the mixture was stirred over 20 min. Polymer films were prepared by solution casting onto a PET backing with following drying at ambient temperature over 3 days. Films of 0.20±0.04 mm thickness were obtained.

TABLE EXAMPLE 8.5

| Example | Eudragit RS | Eudragit RL | TEC | Cab-O-Sil M5 | Swell ratio |
|---|---|---|---|---|---|
| 1 | 49.5 | 16.5 | 30 | 4 | 2.2 |
| 2 | 46.5 | 15.5 | 30 | 8 | 2.8 |
| 3 | 43.5 | 14.5 | 30 | 12 | 3.8 |

The value of Swell Ratio featured for parent Eudragit RL/RS-TEC blend is around 2.0. As the data in Tables Ex. 8.3-8.5 have shown, the hydrophilization of the blends with crosslinked water absorbents such as Carbopol 974, Kollidon CLM and Cab-O-Sil M5 results only in comparatively insignificant increase in Swell Ratio. This is most likely due to very low water permeability of hydrophobic film based on Eudragit RL/RS polymers. However, the materials described in the Examples 8-3-8.5 may be useful as a carriers of hydrogen peroxided solution in teeth whitening strips. For this purpose, the hydrophilic filler (Carbopol 974, Kollidon CLM or Cab-O-Sil M5) should be impregnated with the hydrogen peroxide solution before incorporation into the Eudragit RL/RS film. This film provides good tack and adhesion toward hydrated tooth surface.

EXAMPLE 9

Performance Properties of Adhesive Compositions Based on Interpolymer Complexes Compared to the Properties of Conventional Pressure Sensitive Adhesives and Bioadhesives The properties of the triple blend hydrogels of the invention (PVP-PEG-Eudragit L 100-55), were compared with those of the PVP-PEG binary blends, described in U.S. Pat. No. 6,576,712, and with those of conventional pressure sensitive adhesives ("PSA"; DURO-TAK® 34-4230, National Starch and Chemicals) and classical bioadhesives (covalently crosslinked polyacrylic acid polymers Carbopol® 974P and Noveon® AA1, both from B.F. Goodrich, Co.).

Adhesives based on interpolymer complexes compared to hydrophobic PSAs and bioadhesives

| Attribute | PSA | Bioadhesives | water soluble U.S. Pat. No. 6,576,712 | hydrophilic Examples 1-8 | amphiphilic Examples 9-12 |
|---|---|---|---|---|---|
| ADHESION, $N/_M$ in dry state in hydrated state | 300-600 None | None 10-60 | 370-550 50-70 300-550 | 10-30 100-300 | 140-710 |
| _UBILITY IN WATER | Insoluble | Insoluble, Swellable | Soluble | Insoluble, Swellable | Insoluble, Swellable |
| Water sorption capacity | Less 1% | 98% | Non limited | 96% | 17-85% |
| Film-forming capability | Yes | No | Yes | Yes | Yes |
| Elasticity modulus, Pa $\times 10^5$ | 1.0-5.0 | 0.09-0.9 | 1.3-5.0 | 0.4-40 | 1.0-7.3 |
| MAXIMUM [?] | 22 | More than 30 | 22 | 2.7 | 1.71 |
| Ultimate tensile strength, MPa | 16 | 0.01 | 12 | 30.4 | 5 |
| Logarithm Yield stress, MPa | 4.1 | 2.6 | 3.7-4.9 | 5.0 | Not Available |

PSAs, exemplified above by the SIS block-copolymer based DURO-TAK® 34-4230 adhesive, represent a special class of viscoelastic polymers. They are capable of forming a strong adhesive bond with various substrates under application of a slight external pressure over a short time (1-2 seconds). It is noteworthy that the typical PSAs for human use are mainly based on hydrophobic elastomers with low glass transition temperatures, ranging from −120 to −30° C., which are usually increased by addition of tackifying resins. The common property of the PSAs is a loss of adhesion as the surface of a substrate is moistened. For this reason, conventional PSAs cannot be used for application to highly hydrated and soft biological tissues such as oral Mucosa. For this purpose, hydrophilic bioadhesives are usually employed, which are generally nontacky in the dry state, but adhere to wet substrates. The adhesive strength of such bioadhesives, however is usually much lower than that of the PSAs.

As is seen from this data, the adhesives of various hydrophilic-hydrophobic balances outlined by present invention and obtained by non-covalent crosslinking of film-forming hydrophilic polymers share the properties of both pressure sensitive adhesives and bioadhesives. Indeed, while their adhesive strength is typical of the PSAs, it has increased adhesion towards moistened substrate like bioadhesives. Varying the hydrogel composition and degree of ionization of ionogenic polymers can easily provide the further control of adhesive, water sorption and mechanical properties of the products based on non-covalently crosslinked hydrogels.

Figure 24:
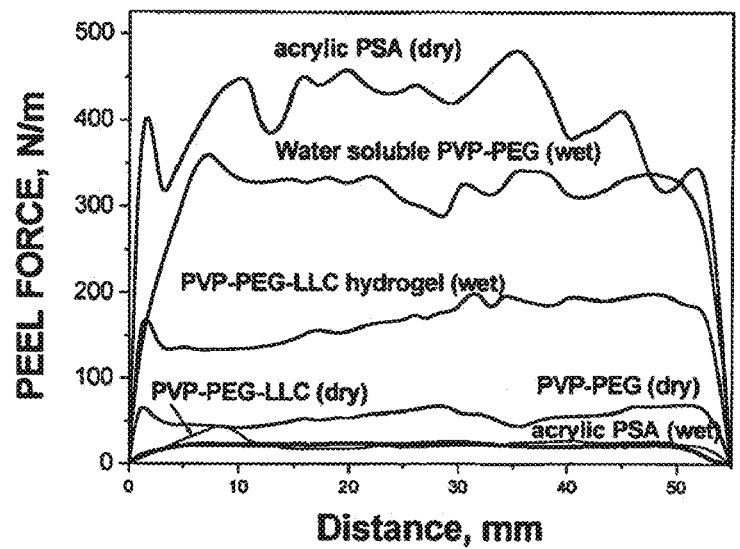
FIG. 24 demonstrates peel force traces towards dry and wet human skin for Gelva acrylic PSA, water soluble adhesive based on carcass-like PVP-PEG complex outlined by U.S. Pat. No. 6,576,712, hydrophilic PVP-PEG-Eudragit L-100-55 adhesive and amphiphilic adhesive based on the ladder-like Eudragit E-100-Eudragit L-100-55 complex (Example 1).
Figure 25:
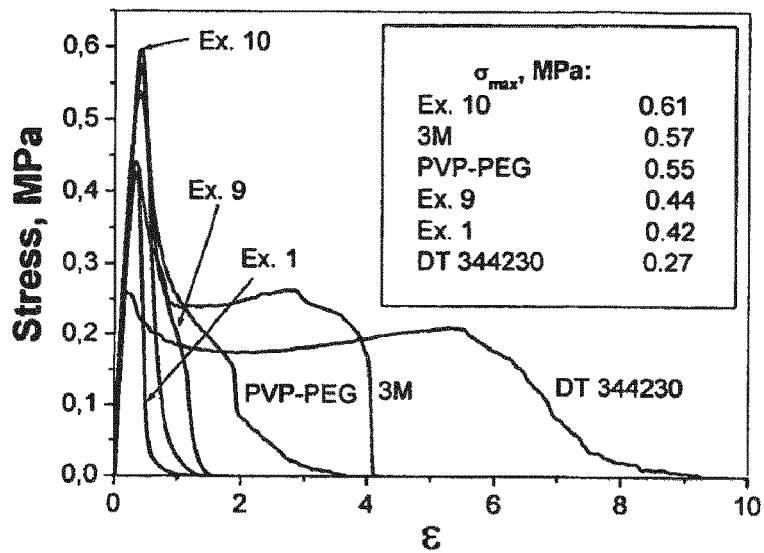
FIG. 25 represents probe tack stress-strain curves for water soluble PVP-PEG (36%) adhesive outlined by U.S. Pat. No. 6,576,712, amphiphilic adhesives described in Example 9 (35% TEC) and in Example 10 (7% of tackifier, 30% TEC), hydrophilic PVP-PEG-Eudragit L-100-55 adhesive at 17% of absorbed water in comparison with two grades of conventional PSAs: SIS-based DURO-TAK®, 34-4230 and acrylic PSA manufactured by 3M.

FIG. 24 compares the peel adhesion towards dry and moistened human forearm skin in vivo for conventional acrylic PSA and three grades of adhesives based on interpolymer complexes. According to these data, the adhesive properties of polymer composites described in present invention and in U.S. Pat. No. 6,576,712 share the properties of PSAs and bioadhesives by combining high adhesion featured for conventional PSAs with capability to adhere to moistened skin and biological tissues typical of bioadhesives, Stress-strain curves obtained in the course of Probe Tack Test are much more informative on the mechanisms of adhesive debonding than the peel force traces presented in FIG. 21. In FIG. 25 the adhesive behaviors of water-soluble PVP-PEG adhesives (described in U.S. Pat. No. 6,576,712 by Feldstein et al.), PVP-PEG-Eudragit L-100-55 adhesive hydrogels (Examples 1-4) and the amphiphilic Eudragit E-100-Eudragit L-100-55 adhesives plasticized by TEC and filled with tackifier Rosin (Example 10) have been compared with the properties of two different grades of conventional PSAs: SIS-based DURO-TAK® 34-4230 PSA and acrylic PSA (3M).

Being expressed in terms of maximum stress under debonding, the tack of adhesives based on interpolymer complexes is comparable with that typical of conventional PSAs. However, the distinctive feature of the adhesive blends described in this invention is the lower values of maximum elongation that results from non-covalent crosslinking of the chains of film-forming polymer. Because the carcass-like crosslinking is significantly looser than the ladder-like crosslinking, it is no wonder that the water-soluble PVP-PEG adhesive demonstrates higher stretching at probe detachment than the adhesives involving the ladder-like type of crosslinking. In this connection it is pertinent to note that the main tools to increase fluidity and maximum elongation of the adhesives provided by the ladder-like crosslinking it is the dilution of network density due to mixing with plasticizers, in the course of swelling in water and also the decrease in concentration of the ladder-like crosslinker.

EXAMPLE 10

Preparation of Adhesive Films by Direct Mixing of Polymeric Components Followed by Extrusion The behavior of the hydrophilic and amphiphilic adhesives described in this invention is typical of covalently crosslinked polymers, in contrast to covalently crosslinked systems, however, the adhesives based on interpolymer complexes can be easily prepared using a simpler blending process, and, furthermore, provide film-forming properties that are unattainable using crosslinked polymers.

While above presented formulations were prepared by casting from solutions followed by drying, the adhesive films of the present invention can be also produced by direct mixing the components in dry state followed by extrusion. The mixing was provided using Thermo Haake Mixer, whereas the extrusion was performed with Skania Single-Screw Extruder. The procedures of mixing and extrusion of the major formulations described in this invention are presented below.

I. Preparation of the Compositions Outlined by Example 1

Following blend was prepared:

| | |
|---|---|
| Eudragit E 100 | 68.2 weight % |
| Eudragit L 100-55 | 6.8% |
| TEC | 25.0% |

Procedures of mixing and extrusion are indicated in Tables 10.1 & 10.2:

TABLE EXAMPLE 10.1

| Time, min. | $T_{mixture}$, °C. | N, rpm | Torque N·m | Operation |
|---|---|---|---|---|
| 0-2 | 100 | 30 | 0-25 | Loading of Eudragit E100 |
| 11 | 110 | 30 | 3 | The beginning of loading premix "G"* with a rate of ~1 ml/min |
| 26 | 10-5 | 30 | 0-0.8 | Decrease of temperature |
| 38 | 91 | 30 | 0.7-0.8 | The finishing of loading of premix "G" |
| 47 | 74 | 30 | 3.0 | Closing the mixer chamber |
| 62 | 66 | 60 | 3.0-4.5 | Increase of stirring rate |
| 68 | 67 | 30 | 3-4 | Elevation of temperature to 120° C. |
| 80 | 120 | 0 | — | Stop |

*Premix "G" is Eudragit L-100-55 plasticized with TEC.

TABLE EXAMPLE 10.2

| $T_{zones}$ | $T_{roller}$ | N, rpm | Extrusion speed, mm/c | Reducing step | Pressure, Bar |
|---|---|---|---|---|---|
| 90/90/95 | 100 | 18 | 7.3 | 14 | 31-35 |

The following examples illustrate the applicability of interpolymer complex adhesives for a range of pharmaceutical products,

EXAMPLE 11

Wound Dressings

The following samples illustrate how the hydrogel compositions of this invention may be used for silver-containing antimicrobial wound dressings. Wound dressings were prepared from the following ingredients using either a melt extrusion or casting/drying processes:

| | Composition, wt. % | | | |
|---|---|---|---|---|
| Sample | Film-forming polymer | Ladder-like crosslinker | Carcass-like crosslinker | Silver salt (1%) |
| 11a | Eudragit E-100, 67.2 | Eudragit L 100-55, 6.7 | Triethyl citrate, 25.0 | Silver sulfate |
| 11b | Eudragit L 100-55, 49.5 | PVP, 9.9 | PEG-400, 39.6 | Silver sulfate |
| 11c | Eudragit E-100, 66.9 | Eudragit S-100, 6.7 | Triethyl citrate, 24.9 | Silver sulfate |
| 11d | Eudragit E-100, 67.2 | Eudragit L 100-55, 6.7 | Triethyl citrate, 25.0 | Silver phosphate |

All of the hydrogel samples were insoluble in water and exudate, but were swellable, thus absorbing a great amount of exudate, Sample 11b was initially tacky and maintained a good adhesion toward dry and moderately exudating wounds, but could be removed from the skin without pain by washing with a large amount of water. Samples 11a and 11c possessed a slight initial tack but became nontacky in a swollen state. Accordingly, sample 11b is useful for treatment of pressure, diabetic, arterial and venous ulcers, whereas Samples 6a and 6c are more suited for covering large, wet and infected wounds and burns.

Potentiometric method with Ag ion selective electrode was used to study silver release from anti-microbial dressings. Aqueous solutions of silver nitrate in the concentration range $2.5*10^{-6}$-$10^{-3}$ M were used to calibrate the Ag ion selective electrode. Circular samples (with diameter=1 inch, area=5 cm$^2$) of anti-microbial films were die-cut and laminated to glass plates by means of a double-sided scotch. The glass plate with the Ag release side upwards was placed into a beaker. 50 ml of distilled water was pored into the beaker. The obtained system was covered with a petri-dish and placed into an oven-thermostat at 25±0.2° C. After specified time points the receptor solution in the beaker over the sample was stirred and silver concentration was measured with the Ag ion selective electrode. After measurement the receptor solution was removed and replaced with 50 ml of distilled water. Cumulative Ag release was calculated and expressed in lig per cm$^2$ of the anti-microbial dressing.

Figure 26:
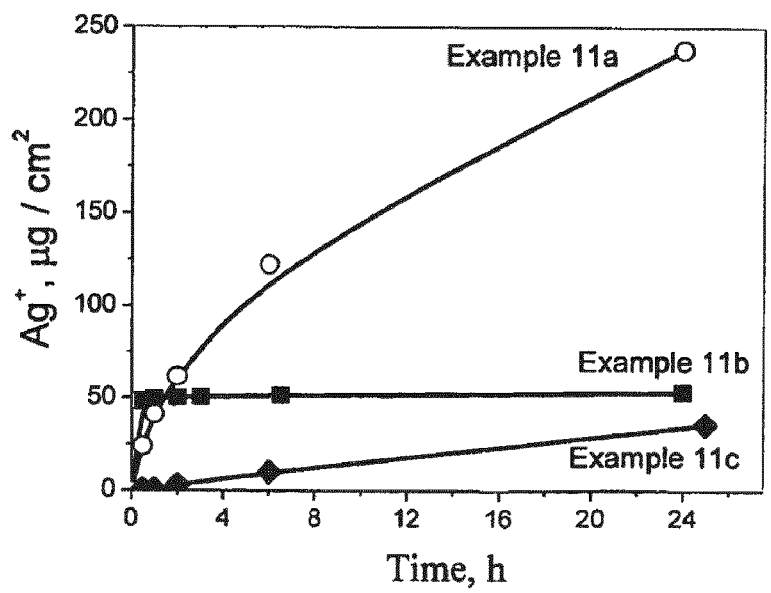
FIG. 26 represents the kinetics of in vitro release of silver sulfate from three adhesive hydrogel compositions used in wound dressings.

FIG. 26 demonstrates how the release kinetics of silver sulfate, as the active agent, from the matrices in vitro were affected by the change in matrix composition. All three hydrogel compositions provided different drug release profiles: Sample 11a delivered the highest amount of silver sulfate; Sample 11b provided a fast release of the active agent during the onset period, followed by a rapid decrease of release rate within steady state stage; and Sample 11c provided zero-order release kinetics. Since various silver salts are characterized with different values of solubility product, it would be expected that different salts of silver, being incorporated into the same hydrogel matrix, may demonstrate different release kinetics.

Figure 27:
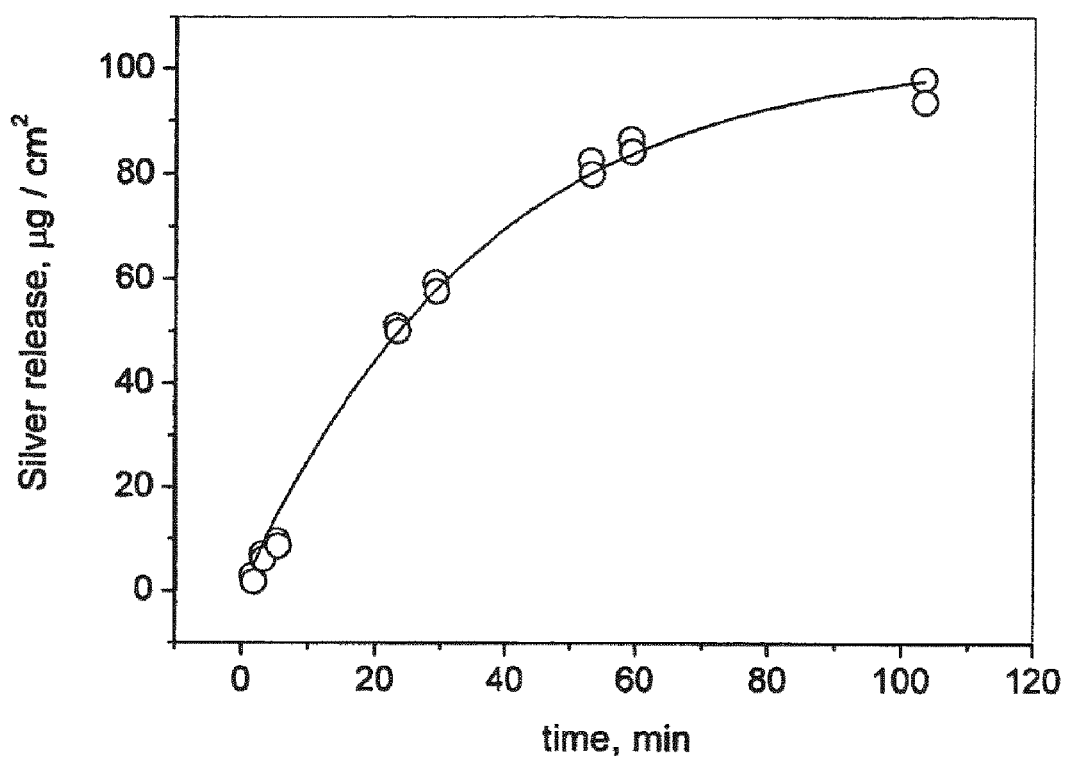
FIG. 27 demonstrates in vitro release kinetics of silver phosphate from the matrix of wound dressing based on the ladder-like interpolymer complex Eudragit E-100-Eudragit L-100-55, plasticized with 25 wt. % of TEC.

FIG. 27 illustrates the effect of silver salts on release profile of Ag ion from the formulation outlined by Example 11d. In this ease the matrix based on Eudragit E-100-Eudragit L-100-55 ladder-like complex was loaded with silver phosphate instead of silver sulfate. Since solubility of silver phosphate in the matrix is about three orders of magnitude lower than that of silver sulfate, the adhesive matrix loaded with silver phosphate provides prolonged release kinetics of anti-microbial agent.

EXAMPLE 12

Slowly Dissolving Matrices with Therapeutic Agents

The following compositions were prepared by dissolution in ethanol of components listed in the Table presented below, casting the solution and drying at temperature of 50° C.

The samples use an acrylate polymer (Eudragit E100) as the film-forming polymer. Sample 12a uses two ladder-like crosslinkers, an acrylate polymer (Eudragit L 10055) and a poly(N-vinyl lactam) (PVP 90), while Sample 12b only includes one ladder-like crosslinker, Eudragit 100-55. Similarly, Sample 12a uses two carcass-like crosslinkers, an alkyl citrate (triethyl citrate) and a polyalkylene glycol (PEG 400), while Sample 12b only includes one carcass-like crosslinker, triethyl citrate.

| Component | Sample 17a (wt %) | Sample 17b (wt %) |
|---|---|---|
| Eudragit E100 | 58.29% | 60.30% |
| Triethyl citrate | 26.10% | 27.00% |
| Eudragit L 100-55 | 2.61% | 2.70% |
| PVP 90 | 2.00% | 0 |
| PEG 400 | 1% | 0 |
| Lidocaine base | 10% | 10% |
| Total | 100% | 100% |

EXAMPLE 13

Liquid Film-Forming Bandages

Samples 13a-13d represent liquid compositions suitable for application to skit as liquid bandages. Sample 13a is a liquid formulation for tooth whitening which contains the insoluble film-forming polymer (Eudragit RS) and plasticizer for this polymer tributylcitrate (TBC). Eudragit RS is a copolymer of trimethylammonioethylmethacrylate chloride (0.1) with ethylaerylate (1) and methylmethacrylate (2), available from Rohm Pharma Polymers. Samples 13b-13d contain no ladder-like crosslinker for the hydrophilic polymer, Eudragit L 100-55. Actually, the ladder-like crosslinker makes the polymer film insoluble. However, for the compositions containing Eudragit RS as a film-forming polymer, the ladder-like crosslinker of PVP was not a necessary component, because the blend is not soluble.

Sample 13e is a film-forming liquid formulation suitable for the treatment of cold sores and canker sores. It contains Eudragit E-100 as a soluble film-forming polymer instead of PVP. Correspondingly, PEG-400 is omitted from the formulation, because TBC is a good plasticizer for both Eudragit RS and E-100.

Liquid bandage and cold sore compositions for skin applications (Samples 10a-10e) may also contain active agents such as local anesthetics. Suitable local anesthetics include dibucaine hydrochloride; dibucaine; lidocaine hydrochloride; lidocaine; benzocaine; p-butylaminobenzoic acid 2-(diethylamino)ethyl ester hydrochloride; procaine hydrochloride; tetracaine hydrochloride; chloroprocaine hydrochloride; oxyprocaine hydrochloride; mepivacaine; cocaine hydrochloride; and piperocaine hydrochloride.

Any natural or synthetic flavorants, such as those described in Chemicals Used in Food Processing, Pub. No. 1274, National Academy of Sciences, pages 63-258, can be included in the compositions of the invention. Suitable flavorants include wintergreen, peppermint, spearmint, menthol, fruit flavors, vanilla, cinnamon, spices, flavor oils (oil of cloves) and oleoresins, as known in the art, as well as combinations thereof. The amount of flavorant employed is normally a matter of preference, subject to such factors as flavor type, individual flavor, and strength desired.

Samples 13c and 13e contain also a skin softening agent such as glycerol monooleate (Peceol, Gattefosse, France).

| Sample | Insoluble film-forming polymer (A) | Plasticizer for (A) | Soluble film-forming polymer (B) | Ladder-like crosslinker for (B) | Carcass-like crosslinker for (B) | Additives | Solvent |
|---|---|---|---|---|---|---|---|
| 13a (Liquid Bandage) | Eudragit RS, 29.00 | TBC, 2.50 | PVP K-90, 3.00 | Eudragit L 100-55, 2.20 | PEG, 3.00 | Sodium 'Citrate, 2.50 | Ethanol, 38.20 |
| 13b (Liquid Bandage) | Eudragit RS, 35.11 | TBC, 11.70 | PVP K-90, 0.36 | — | PEG, 0.18 | — | Ethanol, 52.65 |
| 13c (Liquid Bandage) | Eudragit RS, 20.06 | TBC, 6.69 | PVP K-90, 0.21 | — | PEG, 3.00; 1,2-Propylene Glycol, 28.57 | GMO, 14.29 | Ethanol, 30.09 |
| 13d (Liquid Bandage) | Eudragit RS, 7.95 | TBC, 4.55 | PVP K-17, 1.14 | — | PEG, 1.14 | — | Ethanol, 35.00 |
| 13e (Cold Sore) | Eudragit RS, 33.00 | TBC, 11.00 | Eudragit E-100, 11.00 | — | — | GMO, 10.00 | Ethanol, 44.00 |

The invention claimed is:

1. A method for improving the adhesion of a water-insoluble, water-absorbent adhesive composition, by combining, under conditions effective to form a substantially homogeneous admixture:
   (a) a film-forming, hydrophilic polymer (FFHP) containing a plurality of recurring polar groups, the FFHP selected from the group consisting of poly(dialkyl aminoalkyl acrylates), poly(dialkylaminoalkyl methacrylates), poly(N,N-dialkyl acrylamides), polyvinyl amine), poly(alkylene imine), poly(N-vinyl acrylamide), poly(N-vinyl alkylacrylamides), poly(trimethylammonioethyl methacrylate), poly(N-vinyl lactams), chitosan, copolymers thereof, and combinations of any of the foregoing;
   (b) a complementary multifunctional polymer (CMP) containing a plurality of recurring functional groups, the CMP selected from the group consisting of poly(acrylic acid), poly(methacrylic acid), poly(maleic acid), poly(sulfonic acid), poly(vinyl alcohol), poly(vinyl phenol), poly(ethylene oxide), poly(hydroxyalkyl methacrylates), cellulose derivatives, alginic acid, copolymers thereof, and combinations of any of the foregoing;
   wherein the CMP has a molecular weight lower than the molecular weight of the FFHP, and the FFHP and the CMP are selected such that functional groups contained in the CMP are capable of non-covalently binding to recurring polar groups in the FFHP, and where at least one of the FFHP and the CMP possesses ionogenic groups,
   (c) a plasticizer capable of plasticizing the FFHP, the plasticizer selected from the group consisting of dialkyl phthalates, dicycloalkyl phthalates, diaryl phthalates, mixed alkyl-aryl phthalates, alkyl phosphates, aryl phosphates, alkyl citrates, citrate esters, alkyl adipates, dialkyl tartrates, dialkyl sebacates, dialkyl succinates, alkyl glycolates, alkyl glycerolates, glycol esters, glycerol esters, and mixtures thereof,
   (d) a solvent in an amount effective to provide a solution, the improvement comprising:
   (i) choosing a weight fraction amount of the FFHP that is greater than the weight fraction amount of either the CMP or the plasticizer,
   (ii) adding to the solution, or to the FFHP or CMP prior to the choosing step, an ionizing agent in an amount effective to ionize from about 5% to about 10% of the ionogenic groups in the solution or in the FFHP and/or CMP respectively,
   (iii) casting the resulting solution from (d) onto a substrate, and
   (iv) heating the solution-coated substrate to volatilize the solvent;
   wherein the resulting adhesive composition from (iv) displays an adhesion that is enhanced over the adhesion for the same composition absent the ionizing agent.

2. The method of claim 1, wherein the plasticizer is selected from the group consisting of dimethyl phthalate, diethyl phthalate, dipropyl phthalate, di(2-ethylhexyl)phthalate, di-isopropyl phthalate, diaryl phthalate, dicapryl phthalate, tributyl phosphate, trioctyl phosphate, tricresyl phosphate, triphenyl phosphate, trimethyl citrate, triethyl citrate, tributyl citrate, acetyl triethyl citrate, trihexyl citrate, dioctyl adipate, diethyl adipate, di(2-methylethyl)adipate, dihexyl adipate, diethyl tartrate, dibutyl tartrate, diethyl sebacate, dipropyl sebacate, dinonyl sebacate, diethyl succinate, dibutyl succinate, glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate, triethylene glycol dipropionate, and mixtures thereof.

3. The method of claim 2, wherein the plasticizer is selected from the group consisting of tributyl phosphate, trioctyl phosphate, triphenyl phosphate, trimethyl citrate, triethyl citrate, and tributyl citrate.

4. The method of claim 1, wherein the molecular weight of the FFHP is in the range of approximately 20,000 to 3,000,000 Da.

5. The method of claim 4, wherein the molecular weight of the FFHP is in the range of approximately 100,000 to 2,000,000 Da.

6. The method of claim 5, wherein the molecular weight of the FFHP is in the range of approximately 100,000 to 1,500,000 Da.

7. The method of claim 1, wherein the molecular weight of the CMP is in the range of approximately 10,000 to 1,000,000 Da.

8. The method of claim 7, wherein the molecular weight of the CMP is in the range of approximately 100,000 to 1,000,000 Da.

9. The method of claim 1, wherein:

the FFHP is selected from the group consisting of poly(dialkyl aminoalkyl acrylates), poly(dialkyl aminoalkyl methacrylates), poly(N,N-dialkyl acrylamides), poly(trimethylammonioethyl methacrylate), poly(N-vinyl lactams), copolymers thereof, and combinations of any of the foregoing; and the CMP is selected from the group consisting of poly(acrylic acid), poly(methacrylic acid), poly(maleic acid), poly(hydroxyalkyl methacrylates), cellulose derivatives, copolymers thereof, and combinations of any of the foregoing.

10. The method of claim 1, further comprising combining at least one optional additive with the FFHP, the CMP, and the plasticizer during formation of the admixture.

11. The method of claim 10, wherein the at least one additive includes an active agent.

12. The method of claim 11, wherein the at least one additive is a pharmacologically active agent.

13. The method of claim 12, wherein the pharmacologically active agent is a drug.

14. The method of claim 11, wherein the at least one additive is a cosmeceutically active agent.

15. The method of claim 14, wherein the cosmeceutically active agent is a tooth whitening agent.

16. The method of claim 10, wherein the at least one additive is selected from the group consisting of fillers, pH regulating agents, tackifiers, electrolytes, antimicrobial agents, antioxidants, preservatives, colorants, and combinations thereof.

* * * * *

UNITED STATES PATENT AND TRADEMARK OFFICE
CERTIFICATE OF CORRECTION

PATENT NO. : 8,273,405 B2
APPLICATION NO. : 13/269465
DATED : September 25, 2012
INVENTOR(S) : Feldstein et al.

It is certified that error appears in the above-identified patent and that said Letters Patent is hereby corrected as shown below:

Title page under Item (73) Assignees: change "A.V. Topcheiv Institute of Petrochemical Synthesis, Russian Academy of Sciences" to --A.V. Topchiev Institute of Petrochemical Synthesis, Russian Academy of Sciences--

Signed and Sealed this
Twenty-first Day of May, 2013

Teresa Stanek Rea
*Acting Director of the United States Patent and Trademark Office*